United States Patent [19]

Torrisi et al.

[11] Patent Number: 4,587,666
[45] Date of Patent: May 6, 1986

[54] SYSTEM AND A METHOD FOR MOUNTING FILM TO A SAMPLE HOLDER FOR X-RAY SPECTROSCOPIC FLUORESCENCE ANALYSIS

[75] Inventors: Angelo M. Torrisi, 10 Anpell Dr., Scarsdale, N.Y. 10583; Roland Urbano, Tuckahoe, N.Y.

[73] Assignee: Angelo M. Torrisi, Scarsdale, N.Y.

[21] Appl. No.: 606,565

[22] Filed: May 3, 1984

[51] Int. Cl.⁴ .................... G01N 23/223; G01T 1/36; H05G 1/00
[52] U.S. Cl. ...................................... 378/47; 378/45; 378/208
[58] Field of Search ........................... 378/45, 47, 208

[56] References Cited

U.S. PATENT DOCUMENTS

| | | | |
|---|---|---|---|
| 3,218,459 | 11/1965 | Bens | 378/47 |
| 3,378,684 | 4/1968 | Mentink et al. | 378/47 |
| 4,037,109 | 7/1977 | Hosokawa et al. | 378/45 |
| 4,115,689 | 9/1978 | Won | 378/47 |
| 4,448,311 | 5/1984 | Houser | 378/208 |

Primary Examiner—Richard L. Schilling
Attorney, Agent, or Firm—Paul J. Sutton

[57] ABSTRACT

A system and a method for mounting a thin transparent film across the open face of a sample holder for X-ray spectroscopic fluorescence analysis. The system includes a flexible, tapered cylindrical ring member snap-mounted over a matching tapered portion of an annular wall of the holder body which presses a first portion of the skirt of the film against the tapered annular wall. An outer cylindrical closure sleeve snap-mounted to the annular wall presses additional portions of the film skirt against the annular wall. A rim flange of the closure sleeve holds the ring member in position. An optional O-ring snap-mounted to the annular wall of the holder body presses another portion of the film skirt to the holder body. The method includes sliding the ring member over and snap-mounting it to the holder body followed by passing the closure sleeve over the ring member and snap-mounting it to the holder body so as to position and tauten the film in stages. The optional O-ring is mounted to the holder body prior to the ring member. An assembly block for mounting the film is included.

36 Claims, 21 Drawing Figures

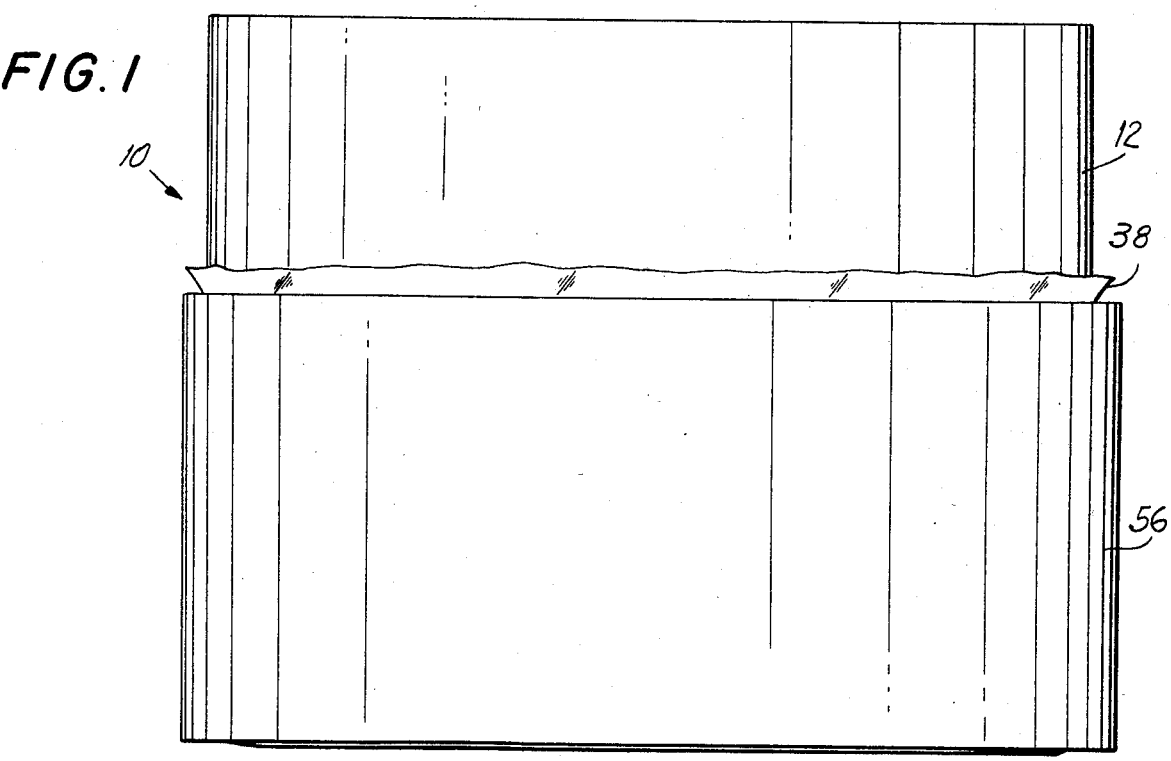
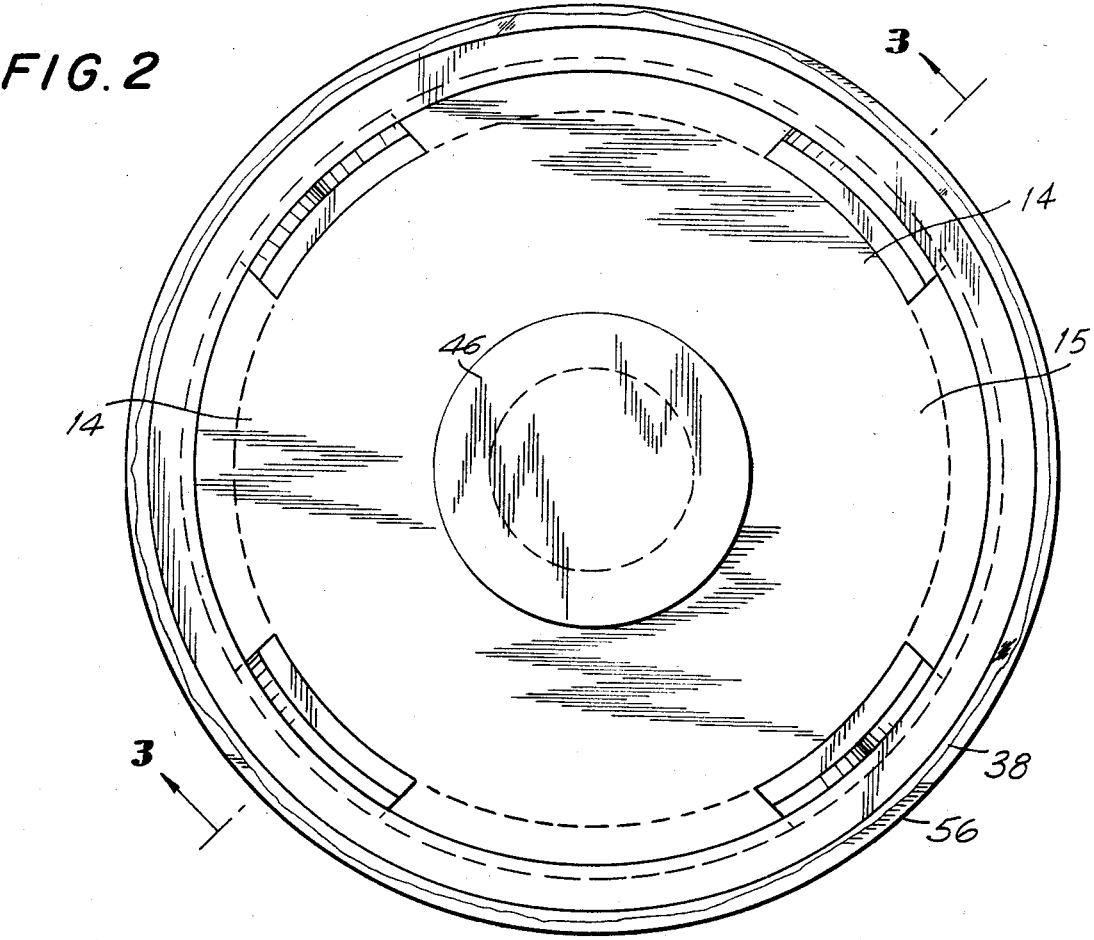

SYSTEM AND A METHOD FOR MOUNTING FILM TO A SAMPLE HOLDER FOR X-RAY SPECTROSCOPIC FLUORESCENCE ANALYSIS

This invention relates generally to the field of disposable sample holders for X-Ray spectroscopic analysis and more particularly to a film handling, positioning, and locking system and method for securing the film covering one face of the sample holder.

The field of spectroscopy involves the measurement of the spectra of certain material being analyzed. Without going into detail here, which is well-known to those familiar with the art, it can in summary be said that an atom releases a quantum of energy that emits a definite wavelength of the electromagnetic spectrum when bombarded by X-Rays. The spectroscope measures the energy or wavelength radiation emitted by a sample material and so verifies the qualitative and/or quantitative presence or absence of certain elements which generally are within a defined range associated with the sample being analyzed. The sample may be of any liquid, slurry, powder material, or as made possible by this invention even industrial gases that can occur in the run of industry. Gasoline and oils are examples of liquid materials that are often analyzed and often a suspected contaminate is the object of the analysis; or the spectroscope may be a tool of the inorganic analysis of a sample such as a mineral ore powder.

The field of spectroscopy is that of high precision technology. The X-Ray apparatus that is used to bombard the sample is finally dependent upon the quality of the presentation and preparation of the sample being analyzed because a precise geometry of distance is involved in the measurement process. Also, because of X-Ray absorption factors, polyethylene or polypropylene films employed as X-Ray transparent windows are fragile and very thin, ranging in thicknesses as low as between 0.00010 in. (0.002 mm) to 0.00050 in. (0.013 mm).

A sample is positioned in a cylindrical sample holder that includes a holder body forming a cell adapted to contain the sample. A disposable sample holder is generally made of polyethylene or polypropylene and is generally intended to be discarded after a single use. A sample holder will range in size between diameters of 1 in. to 2 in. (25 mm to 57 mm) and have a height of about 1 in. (25 mm), although these dimensions will vary.

The first phase of the analysis is in the support and presentation of the sample for spectroscopy. In one type of holder, a very thin plastic film is placed taut as an X-Ray transparent window across the circular end face of the body of the holder, and the skirt of the film is then secured to the outer wall of the body. The body is then inverted so that the window film face is positioned downwards. The holder cell is thereupon filled with the sample through the top open face of the holder body. A cap is then placed on the top open face to close the cell and form a complete holder of a body with a cap. The sample holder is then placed in a cell positioner of the particular spectroscopic apparatus being used and the X-Rays are applied to the downward film face of the holder upon which the sample material is lying. The X-Ray analysis may be conducted in an air, inert gas, or vacuum environment; if the sample material is to be analyzed in a vacuum, then the top wall, or cap side, of the sample holder must be vented so that the pressure in the cell does not cause the film to bulge across the lower face of the holder and so compromise the geometric precision of the measurement. Venting is accomplished in the type of sample holder being discussed by the placement of a vented cap that cooperates with structure in the body of the holder to pass air of the cell. In certain cases where air is to be replaced by another gas, such as an inert gas, the same procedure is followed. Venting is made practical in the cases of high viscosity liquids and high density powders by a baffle arrangement in the cap and holder that prevents these materials from escaping from the cell by creating a path that easily passes a gas but sets up an obstacle for the materials. The body of a holder that is being used in a venting process preferably forms a top well that can receive any overflow of a liquid sample that exudes through the baffled vent. In the case of spectroscopic analysis of a sample that need not be vented, the top cap and the body preferably form a seal between them.

The precise geometry of distance encompassed by spectroscopic analysis is dependent upon the the integrity of the film face that is tautly stretched across the bottom face of the cell of the holder. The sample material is in the cell and lies upon the film, which must retain a perfectly flat horizontal face, which in turn creates a perfectly flat surface of the sample material lying on the film. In addition, the film must maintain a tight pressure fit around the base of the holder so as to create a seal that prevents any leakage of sample material, particularly a liquid or volatile sample, from the cell. Also, film can shrink or expand because of heat generated by X-Ray bombardment. The coefficient of expansion of the film and the sample may vary thus creating stress on the film.

The achievement of a tight fit of the film across the open face of the cell of the holder is attempted in the present state of the art by securing the skirt of the film by a pressure fit of a cylindrical member against the outer base of the holder body. At one time a common means of doing this was by passing an 0-Ring around the skirt of the film and the annular body of a holder into a snap-on connection with the film skirt wedged into the snap-in slot on the upper annular holder body. After the O-ring has been positioned over the body and the skirt of the film, the edges of the skirt are then pulled so as to make the film at the face taut. The pressure made by the O-ring maintains the tautness. Another method of achieving and maintaining film tautness and sealing is to place a thick walled, rigid cylindrical film ring around the skirt of the film in combination with the O-ring. The rigid film ring is placed around the base of the holder body so that it presses the film tightly across the face of the body. The rigid film ring is spaced from the O-ring, which further secures the skirt of the film. The rigid film ring is locked to the body preferably by a snap-in connection. Determination of closeness of fit of the rigid film ring to the base of the holder body is the result of a compromise; very close fit of film ring to holder body may produce a good seal but at substantial risk of film rupture; while a loose fit of film ring to holder body may minimize danger of rupture but at risk of leakage and lack of tautness.

The present state of the art does not permit routine, safe creation of a liquid tight or air tight sample cell holders.

There are two serious problems in creating a taut fit of the film by means of the present technology.

The first problem is that when the skirt of the film is drawn from around the O-ring in order to create film tautness across the film face, or when the snap in connection on the inner surface of the rigid film ring is drawn across the skirt of the film, the film can be ruptured or torn at the base of the holder. Rupturing of the film around its edges can have undesirable results. One is that the work of preparation must be redone, but an even more serious problem is that often such a tear is so minute that it is not detected and the sample is placed in the cell with the slightly torn film. The result is that the sample, particularly a liquid or volatile sample, will leak from the cell. If the leakage occurs during the time the sample holder is in the cell positioner of the spectroscope array, it can result in damage to the equipment.

Yet another problem of the present art is the lack of durability of maintenance characteristics of the film face or the film seal. If the film face is not maintainable taut, then the mounting of the film to the holder must be done by the technician at the testing apparatus, and the holders cannot be prepared in lots on a mass production basis by non-technical personnel either at the laboratory site or at the manufacturer. And if the seal of the film is not maintainable, then, when the sample material demands a sealed cell condition with a sealed cap or a sealed film face, the sample material may leak out, or be drawn out by capillary action, or undergo a matrix change either because of evaporation in the cell or chemical change from ambient air in the cell. In any case, the X-ray analysis will be compromised. For this reason, with the present state of the art, once the sample material has been placed in the cell, the analysis procedure must follow quickly within a few minutes.

One special type of sealed sample holder mounts a filter paper impregnated with a liquid sample to be analyzed by X-ray analysis. The filter paper is positioned at the center of the face of the cell holder and is sandwiched between a pair of layers of film that are locked to the outer wall of the sample holder to maintain tautness of both layers of film across the cell face.

The present invention contemplates a gentle film handling, positioning, and locking system for the film of a sample holder for X-ray spectroscopic analysis that overcomes the limitations and disadvantages of the prior art by substituting for the currently used rigid film ring with its rigid locking ring, a flexible, thin walled cylindrical film ring tapered to match the annular cell body wall with a soft, flexible inner protruding locking ring at its leading edge, by positioning this film ring at a distance from the cell face, and by providing an outer sleeve member that both tightens the film tautly across the face of the holder body and maintains the tautness indefinitely and in addition seals the face of the cell.

Accordingly, it is an object of the present invention to provide a gentle, firm film handling, positioning, and locking system for film for a sample holder that tautens the skirt of the film against the lower face of the holder by provision of two locking rings and by provision of several gentle, hugging pulls along the length of the skirt, and by concentrating pressure on the film against the entire surface of the skirt.

It is yet a further object of this invention to provide an outer sleeve member that rides over the thin walled, flexible inner film ring and presses the upper and lower periphery of the film skirt against the holder body so that the film maintains its tautness across the face by means of the three close fit parallel surfaces and dual locking rings and further maintains the sealing of the cell of the holder.

It is yet another object of the present invention to provide a film locking system that includes an outer sleeve member that passes over the inner film ring member and thereupon tautens the film by pulling the periphery portion of the skirt against the outer surface of the sample holder during the positioning operations thus tautening the film across the face of the sample holder and also maintaining the seal of the cell of the holder.

It is still another object of this invention to provide a dual film locking triple parallel support system that permits preassembly of the film to the sample holder at a factory or at the laboratory by non-technical personnel without risk of losing the taut condition of the film or the sealing quality of the film.

The present invention fulfills the above objects and overcomes limitations and disadvantages of prior art solutions to problems by providing a novel film handling, positioning, and locking system for a sample holder for liquid, powder, volatile, or gaseous material for X-ray spectroscopic fluorescence analysis. The system includes a substantially cylindrical holder body having a substantially annular wall forming a cell adapted to contain the sample material. The annular wall has a rim portion that defines an open face of the cell. A film layer is positioned across the face of the cell for sealing the face and preventing the passage of sample material from the cell past the face. The film layer also is for maintaining a taut surface for the sample material for the sample analysis. The film layer includes a film skirt that engages with the annular wall of the body. A flexible, thin walled, cylindrical ring member tapered to match the cell body with a flexible inner protruding locking ring at its leading edge is positioned around a first portion of the annular wall of the body associated with the open face. The flexible inner protruding locking ring expands slightly and is for pressing the skirt of the film to the middle portion of the annular wall first, hugging and drawing the film layer across the face sufficient only to achieve a taut surface of the film layer across the face during mounting of the ring to the body, then supporting the film by closely fit tapered cylindrical walls of the ring and body and then locking the film in place when the locking ring contracts upon reaching the locking recess provided in the cell body wall thereafter maintaining the taut surface across the face after mounting. A closure sleeve member is positioned around the annular wall of the body and around the ring member. The sleeve member is closely spaced radially from the ring member. The sleeve member is for pressing the periphery of the skirt to an upper portion of the annular wall disposed adjoining the middle portion and for pressing the periphery of the skirt to the lower portion of the annular wall and through the sliding, pressing action of its inner protruding locking ring and for drawing the film layer to a taut surface across the face of the cell during mounting of the sleeve member to the body. The sleeve member also is for maintaining the taut surface after the mounting. The film ring member is spaced axially inwards from the face of the cell so as to relieve excess pressure against the film at the outer corner of the rim portion. The sleeve member has a circumferential snap-in connection with the annular wall of the body at one annular edge and an inwardly extending flange at the opposite annular edge, the flange engaging the outer annular edge of the ring member to prevent it from moving axially outwardly from the holder body and engaging the lower annular edge of the cell body to firmly support the film between closely fit parallel surfaces including matching curved fit support at the window edge. The sleeve member is radially spaced from the ring member. An optional O-ring is positioned around the annular wall spaced inwardly from the ring member and radially spaced from the sleeve member. The O-ring presses the skirt of the film to the annular wall, pulls the film to a taut surface during mounting, and maintains the taut surface after mounting. The ring member and the sleeve member achieves a double lock of the film with the holder body and a triple film support is achieved with the three sets of closely fit matching surfaces.

A special sealed sample holder includes a double layer of film that sandwiches a filter paper impregnated with liquid sample material at the face of the cell. The inner layer of film is pressed by the ring member, the O-ring, and the sleeve member, while the outer film layer is pressed by the ring member and the sleeve member.

The invention will be more clearly understood from the following description of specific embodiments of the invention together with the accompanying drawings, wherein similar reference characters denote similar elements throughout the several views, and in which:

FIG. 1 is an elevation view of a sample holder with a closure sleeve with a vented cap;

FIG. 2 is a top view of the sample holder;

FIG. 16a is a detailed view of the mounting between the gripper and the fork.

Figure 4:
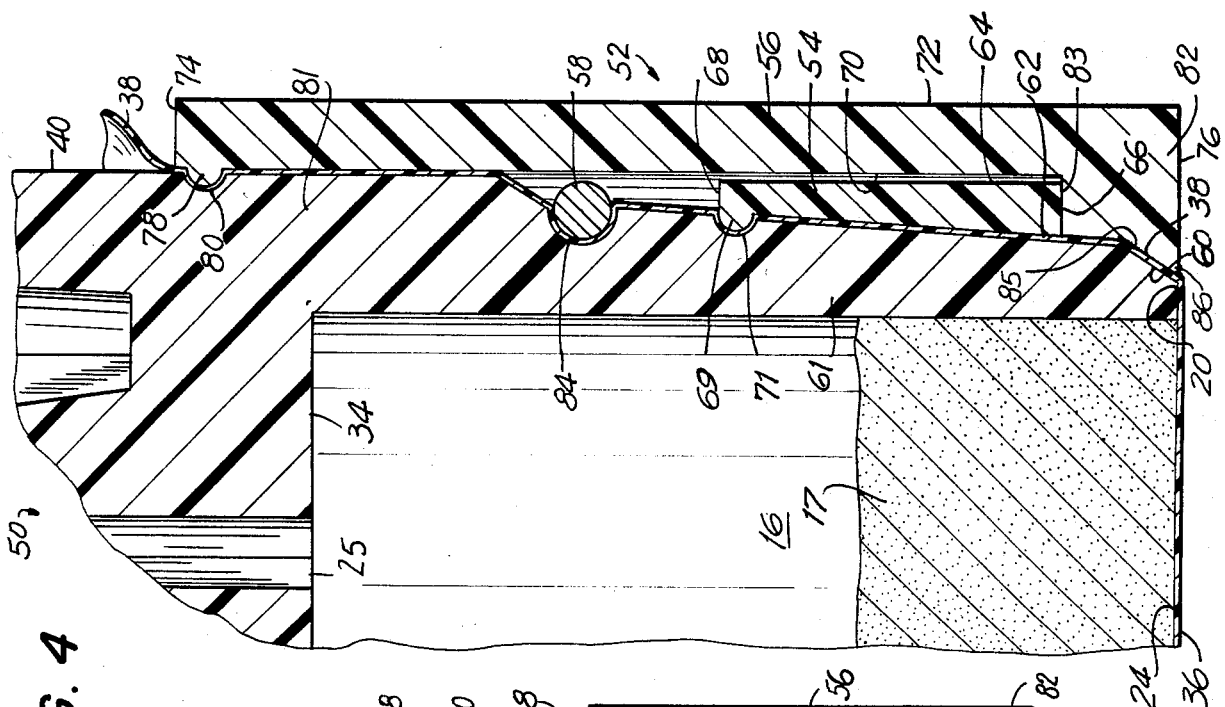
FIG. 4 is an enlarged view of a portion of FIG. 3.

Reference is now made in detail to the drawings wherein reference numerals are correlated to various elements of the invention as described below.

Figure 3:
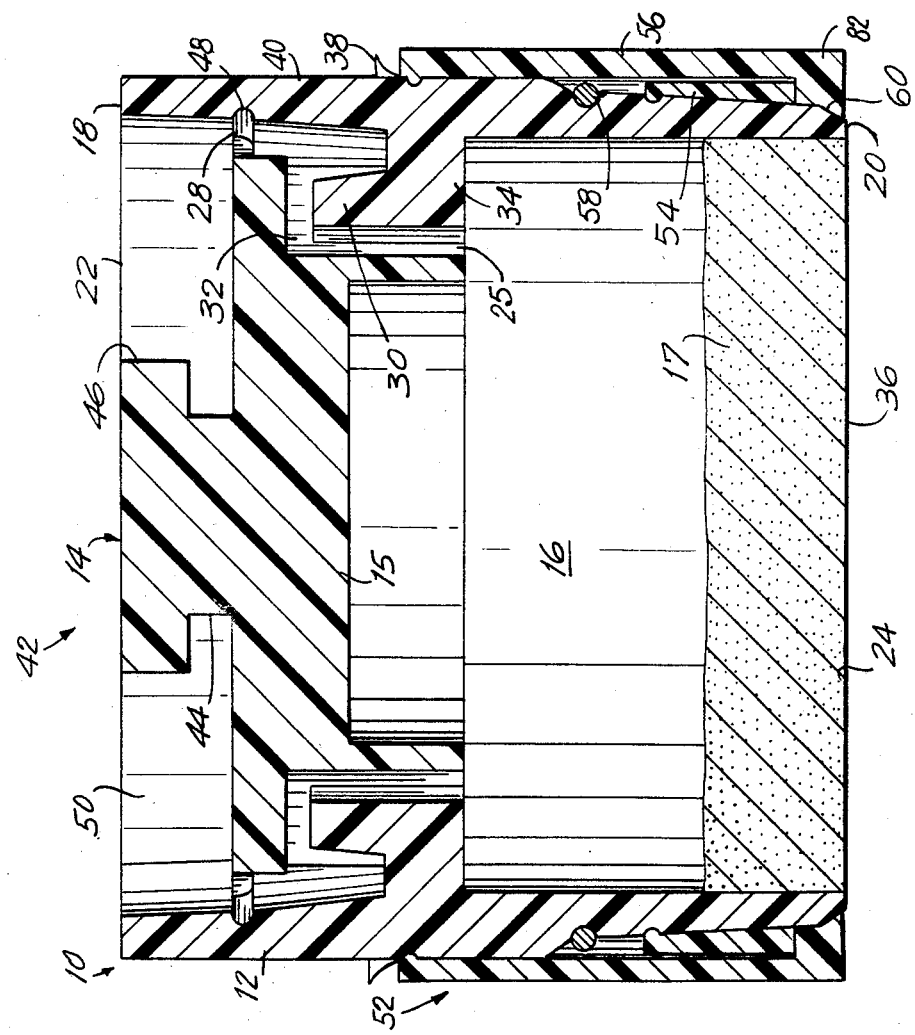
FIG. 3 is a view taken through line 3—3 of FIG. 2.
Figure 6:
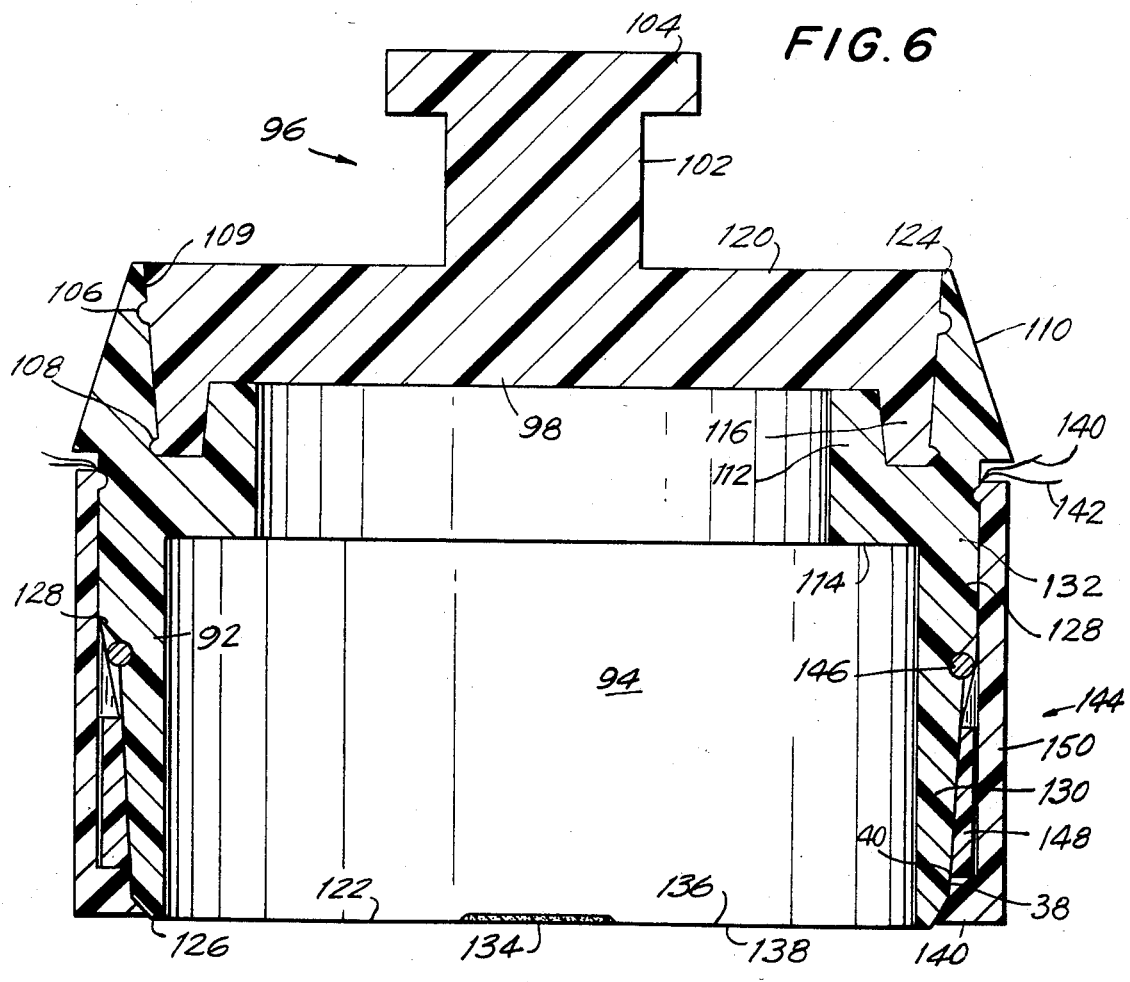
FIG. 6 is a view taken through line 6—6 of FIG. 5.

FIGS. 1 and 2 are elevational and top views of a sample holder 10 including a substantially cylindrical body 12 and a cap 14 removably connected to the top portion of body 12. Cap 14 includes a substantially cylindrical transverse wall 15 set within body 12 forming a substantially cylindrical cell 16 with the outer wall of body 12. A sample material 17 is disposed within cell 16. Sample material 17 is shown as a powdered material for purposes of exposition but it could be a liquid. As shown in FIG. 3, body 12 includes opposed upper and lower circular rims 18 and 20 which form opposed upper and lower open faces 22 and 24 respectively of cell 16. Sample holder 10 is a vented holder, with cap 14 being a vented cap having a baffle system for passing air from cell 16 or passing an inert gas to cell 16 without sucking any portion of sample material 17 at the bottom of cell 16 from the cell in those cases where sample material 17 is high viscosity liquid or a high density powder in the event of a spectroscopic procedure involving a vacuum requirement. FIG. 3 is from a view taken through a pair of opposed baffle vents 28. Body 12 includes an annular upwardly extending flange 30 that fits loosely into an annular slot 32 formed around the bottom periphery of a transverse wall portion 34 that extends across cell 16 so as to completely prevent passage of sample material 26 from cell 16 if cap 14 were seal mounted to body 12 (in a manner analogous to a sealed cap to be discussed as shown in FIG. 6). When the cap is vented as in FIGS. 2 and 3, it is possible that small amounts of liquid can pass from cell 16 by way of the annular U-passage 35 between flange 30 and slot 32 and baffle vent 28. Cell 16 is further defined by a layer of plastic film 36 that lies across lower face 24 of body 12 in such a way as to seal cell 16 across lower face 24. Sample material 17 lies upon film 36. Film 36 includes a skirt portion 38 that extends past lower rim 20 and around the outer wall 40 of body 12. A cap holder 42 comprises a vertical stem 44 and a top disk 46. Cap holder 42 mounted to cylindrical transverse wall 15 gives an operator lifting capability by hand or with a tool. An annular snap-in connection at the top of wall portion 34 secures cap 14 to body 12. Annular flange 30 is disposed at a distance from upper rim 18 so that when cap 14 is in place, wall portion 34 forms a wall 50 with body 12 that is capable of receiving overflow of sample material 17 past baffle vent 28 in the event of sample expansion, excess material, or a spectroscopic procedure involving a vacuum requirement.

A film locking system 52 is shown in FIGS. 3 and 4 that both positions film layer 36 to a taut surface across lower face 24 of cell 16 and in addition maintains the tautness across the lower face indefinitely. Film locking system 52 includes a substantially cylindrical ring member 54, which accomplishes a single lock of film layer 36, a substantially cylindrical closure sleeve member 56, which accomplishes second and third locks of film layer 36, and an optional O-ring member 58, which accomplishes a fourth lock of film layer 36. As will be discussed in relation to the sealed sample holder shown in FIGS. 5, 6, and 7, optional O-ring member 58 may be a requirement. Ring member 54 is flexible and is made of a flexible material, preferably a flexible plastic such as medium density, or medium to high density polyethylene. Sleeve member 56 is made of a semirigid material, preferably a semirigid plastic such as medium to high density polyethylene. O-ring 58 is made of a flexible plastic such as medium density or medium to high density polyethylene.

It is further emphasized that film locking system 52 also positions film layer 36 to a taut surface across lower face 24 to maintain a tight seal around lower rim 20 of body 12 so that sample material 17 will not escape from cell 16.

It is again noted at this time that one of the advantages of film locking system 52 occurs during the placement of film layer 36 onto body 12. After the film is set across lower face 24, skirt portion 38 is drawn around outer wall 40. Skirt portion 38 is pulled upward around outer wall 40 if the assembly block is used for placement of film or skirt portion 38 would be pulled down around outer wall 40 if placement of film is performed manually without the assembly block since lower face 24 and upper face 22 would be reversed in orientation from their positions shown in FIGS. 3 and 4 during unassisted manual mounting of the film.

As seen best in FIG. 4, a circumferential bevel 60 is formed at the intersection of rim 20 and outer wall 40 of body 12. Ring member 54, which forms a cylindrical tapered inner surface 62 that is adapted to fit closely with cylindrical tapered outer wall 40 of body 12, is positioned around a lower portion of outer wall 40, that is, the portion associated with lower face 24. Ring member 54 includes a downward annular end 66 and an opposed upper annular end 68 and an outer surface 64. Ring member 54 is spaced from lower face 24 and lower rim 20 so that film 36 is free from direct pressure at bevel 60. Film is supported by closely fit tapered and curved parallel surfaces of closure sleeve 56 and tapered portion 61 of body 12 between 60 and 66.

As seen most clearly in FIG. 4, circular outer wall 40 of body 12 has an outward taper over a tapered portion 61 from lower rim 20 to a circular position approximately midway between upper and lower rims 18 and 20. Ring member 54 forms a cylindrical tapered inner surface 62 that is adapted to fit closely with tapered portion 61. Ring member 54 includes a substantially vertical cylindrical outer surface 64 and bottom and top annular ends 66 and 68 respectively that extend between inner and outer surfaces 62 and 64. Bottom end 66 of ring member 54 is spaced inwardly from lower face 24 and lower rim 20 of body 12 so that film 36 is free from excessive pressure at bevel 60 as the film is angled from lower face 24 along outer wall 40 of body 12. Ring member 54 preferably is snap-in connected to outer wall 40 by way of a circumferential bead 69 extending inwardly from upper annular end 68 that is adapted to snap into a circumferential groove 71 formed in outer wall 40.

During the mounting process of film 36, skirt portion 38 of film 36 is first drawn against outer wall 40 and ring member 54 is then slipped over lower rim 40 and slid axially inward along outer wall 40 with film skirt 38 being pressed against outer wall 40 during the process. As this occurs, film 36 is pulled taut across lower face 24. The person assembling the film can also lightly pull the peripheral portions of skirt 38 away from lower face 24 in order to flatten out any wrinkled portions of film 36. It is to be particularly pointed out that film 36 at corner 60 is not particular stressed since it is free to slide without being pinched by another member. Film 36 has a certain lubricious quality that allows it to some extent to be slid between outer wall 40 of body 12 and inner surface 62 of ring member 54. Ring member 54 comes to a natural point of rest in its inward movement because of the outward tapers of outer wall 40 of body 12 and inner surface 62 of the ring member; that is, ring member 54 is limited from movement in an axial direction relative body 12 upon its being positioned around lower tapered portion 61 of body 12 relative to lower face 24.

At this point, sleeve member 56 is positioned for mounting to body 12. Sleeve member 56 is cylindrical having cylindrical inner and outer surfaces 70 and 72 respectively and opposed inner and outer, or upper and lower, annular edges 74 and 76 respectively. Inner annular edge 74 is spaced from rim 20 of cell 16 and outer annular edge 74 lies substantially in the same plane as rim 20. An annular flange 82 extends radially inwardly from inner surface 70 of sleeve member 56 generally at outer rim 76. Flange 82 forms an annular inwardly facing stop surface 83 spaced axially inwardly from lower rim 20. Stop surface 83 is in a plane that is substantially parallel to the plane of downward annular end 66 of ring member 54 and is adapted to be in pressing contact with downward annular end 66 so that ring member 54 is aided in being kept in its mounted position around body 12. Annular flange 82 also forms a tapered inner surface 85 that presses film skirt 38 of film 36 against the tapered outer surface of tapered portion 61 of outer wall 40 of body 12 in the area of rim 20. Flange 82 includes an annular radially inwardly extending lip 86 that overlaps annular bevel 60 formed around rim 20 of body 12. Lip 86 also overlaps film 36 at the bevel. Sleeve member 56 is slid over outer wall 40 of body 12 at lower face 20. As is clearly shown in FIG. 4, inner surface 70 of sleeve 56 is axially spaced from outer surface 64 of ring member 54 forming an annular space 73 between them so that closure sleeve 56 slides over ring member 54 without touching. An annular snap-in bead 78 which extends inwardly from inner surface 70 proximate to upper edge 74 is adapted to snap into a connecting position with body 12 into an annular slot 80 formed in outer wall 40 of body 12. Outer wall 40 of body 12 is tapered from lower rim 20 to a point approximately midway to upper rim 18. From the end of the taper to upper rim 18, outer wall 40 extends vertically upwardly at vertical position 81 of outer wall 40.

Bead 78 preferably is spaced from outer surface 64 of ring member 54 during the slipping on of sleeve 56, but a touching between the two elements during the slip on is possible without affecting the utility of the invention. After sleeve 56 is slid past ring member 54, inner surface 70 and bead 78 come into pressing contact with film skirt 38 and pressing contact with outer wall 40 of body 12 through film skirt 38. A gently drawing of skirt 38 and of film 36 across lower face 24 occurs so as to further tauten film 36 across lower face 24. Sleeve 56 connects to body 12 when bead 78 snaps into slot 80 so that film skirt 38 is pressed against vertical wall portion 81 by vertical inner surface 70 of sleeve 54. An annular remnant of skirt 38 is seen extending above upper rim 74 of sleeve 56 in FIG. 4. Once sleeve 56 achieves its final position as shown in FIG. 4, ring member 54 is stopped from moving axially relative to body 12 towards lower rim 24 by action of annular flange 82.

After the final positioning of sleeve 56, film 36 is maintained in its taut position across lower face 24 by the first locking action of inner tapered surface 62, ring member 54 pressing film skirt 38 against the parallel tapered surface of annular outer wall 40; a second locking action of inner tapered surface 85 of flange 82 of sleeve 56 pressing film skirt 38 against the parallel tapered surface of annular outer wall 40 between outer rim 20 of body 12 and downward annular end 66 of ring member 54; and a third locking action of vertical inner surface 70 of sleeve 56 pressing film skirt 38 against the parallel vertical surface of annular outer wall 40 spaced above, or inwardly from, ring member 54. Thus, film 36 is held taut by first, second, and third closely fitting, parallel, consecutive gripping support areas that operate in combination. As viewed in FIGS. 3 and 4, first, second, and third gripping support areas can be described as middle, lower, and upper support areas respectively.

A snap-on lock defined by annular bevel 69 and annular groove 71 holds ring member 54 in position and further operates to grip film 36. A snap-on lock defined by annular bead 78 and annular groove 80 holds sleeve 56 in position and further operates to grip film 36.

An optional fourth locking action of film locking system 52 is accomplished as follows. Outer wall forms an annular groove 84 that lies in a plane substantially parallel to upper and lower faces 22 and 24 of body 12 and is positioned between the second and third gripping areas defined above, that is, between upward rim 68 of ring member 54 and vertical portion 81 of outer wall 40 of body 12. Circumferential O-ring 58 is adapted to be snap-mounted onto body 12 at groove 84. When O-ring 58 is being used, the first step in the mounting process of film 36 onto body 12 is pressing O-ring 58 over body 12 at lower face 24 and passing the O-ring over tapered portion 61 of outer surface 40 to a point proximate to vertical portion 81 where groove 84 is located. During the mounting process of mounting O-ring 58 to body 12, film skirt 38 is lightly pulled as O-ring 58 reaches the outer portions of tapered portion 61. After O-ring 58 is snap-mounted into groove 84, film skirt 38 can be gently pulled so as to tauten film 36 across lower face 24. Once this is accomplished, O-ring 58 acts to maintain film 36 across lower face 24. When O-ring 58 is used together with ring member 54 and sleeve 56, a quadruple lock action of film 36 with body 12 occurs. It is this quadruple lock, or triple lock in the case of O-ring 58 not being used together with the three closely fit parallel surfaces that provide a sealed cell. Because the present invention gives an indefinite period of locking for film 36 to body 12, film 36 can be preassembled by non-technical personnel at a factory or mass preassembled at the laboratory location of spectroscopic analysis.

There is a particular case where an O-ring is needed. This is in the special case of a remote access X-ray sample holder shown in FIGS. 5, 6, and 7, where the sample material is impregnated in a unit of filter paper placed between two layers of film and positioned at the center of the lower cell face. A sealed cell is required. A description of this system follows.

Figure 5:
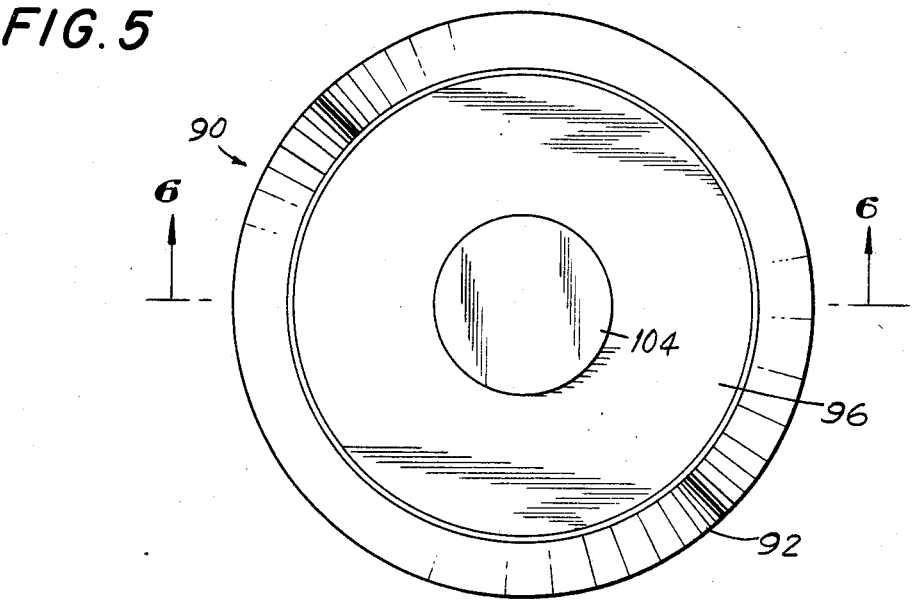
FIG. 5 is a top view of a sample holder with a sealed cap.
Figure 7:
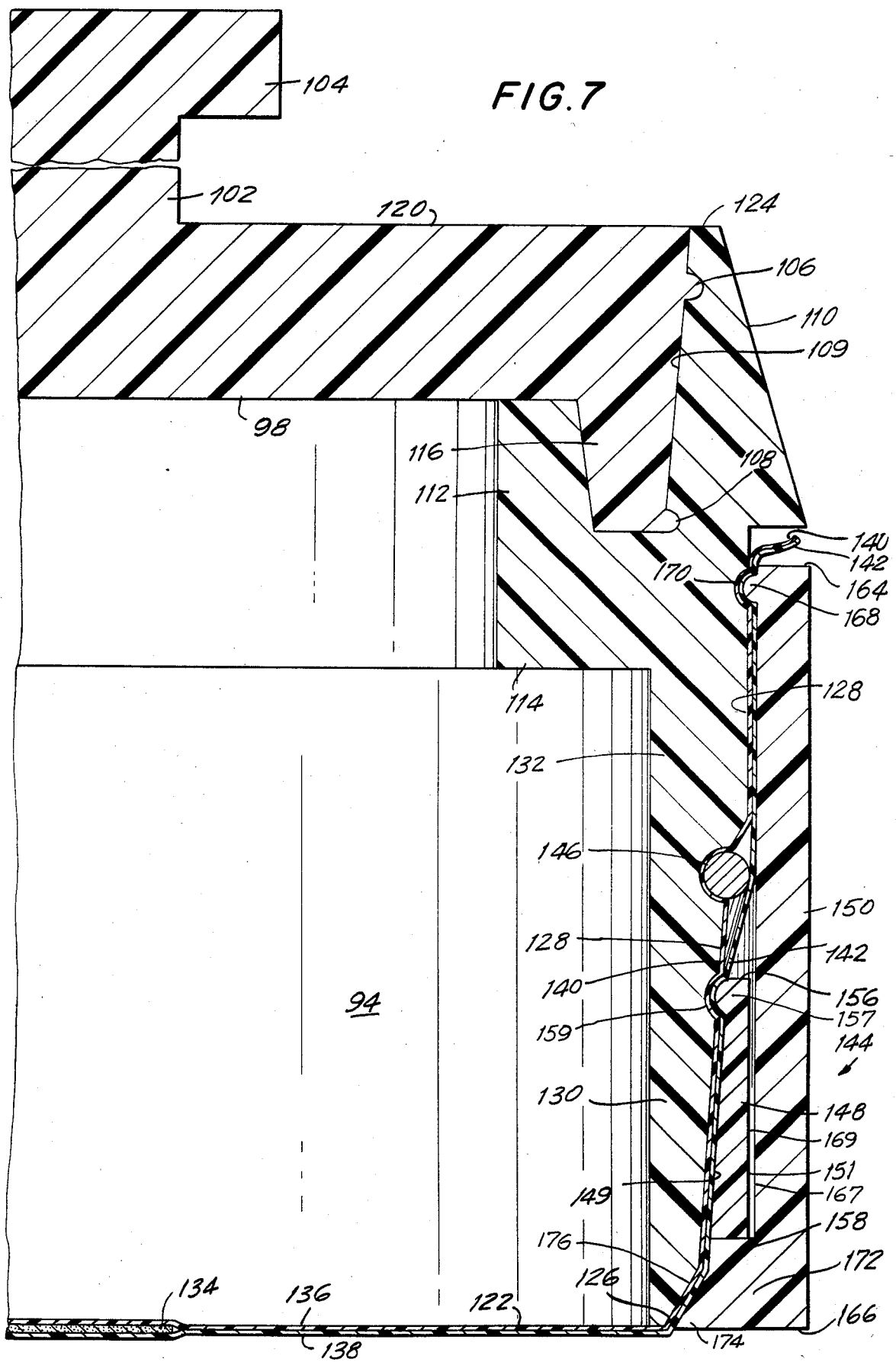
FIG. 7 is an enlarged view of a portion of FIG. 6.

Attention is now directed to FIGS. 5, 6, and 7, where a sealed sample holder 90 is shown including a substantially cylindrical body 92 forming a substantially cylindrical cell 94 and a cap 96 having a transverse sealing wall 98 and a handling support compromising a central stem 102 with a disk top 104. Cap 96 is snap-connected at a pair of upper and lower annular snap-on connections 106 and 108 located at the inner annular surface 109 of an annular wedge 110, which is adapted to press-fit under a cell positioner of a spectroscopic array (not shown). An annular inner flange 112 extending upwardly from an annular support arm 114 forms with surface 109 an annular slot into which a downward annular flange 116 of cap 96 is tightly fitted. Cell 94 of body 12 has opposed upper and lower open faces 120 and 122 respectively which lie in substantially parallel planes and which are defined by upper and lower annular rims 124 and 126 respectively. Upper face 120 as noted earlier is sealed by transverse wall 98 of cap 96.

Body 92 includes an annular outer wall 128 that includes a lower outwardly tapered portion 130 extending from lower rim 126 to an annular line approximately midway to annular wedge 110 and a substantially vertical portion 132 extending approximately from tapered portion 130 to annular wedge 110.

As can be seen most clearly in FIG. 7, a unit of filter paper 134 impregnated with a liquid sample material is positioned at the center of circular lower face 122. Filter paper 134 is sandwiched between inner and outer film layers 136 and 138 respectively, which have inner and outer film skirts 140 and 142 respectively that lie against outer surface 128 of body 92. More precisely, inner film skirt 140 lies against outer wall 128 and outer film skirt 142 lies against inner film skirt 140.

Film handling, positioning, and locking system 144 of sample holder 90 is essentially analogous in construction and arrangement to film handling, positioning, and locking system 52 described in relation to the embodiment shown in FIGS. 1, 2, 3, and 4, and essentially achieves the same purposes.

In summary, film locking system 144 includes an O-ring 146, analogous to O-ring 58 of holder 10, a ring member 148 analogous to ring member 54 of holder 10, and a closure sleeve member 150 analogous to closure sleeve member 56 of holder 10.

The mounting process for holder 90 begins with stretching inner film layer 136 across lower face 122 and holding inner film skirt 140 against outer wall 128. O-ring 146 is passed over lower face 122 and over inner film skirt 140 until the O-ring is snapped into annular groove 152 formed in outer wall 128. At this time inner film skirt 140 is grasped at its periphery and pulled gently so as to tauten inner film layer 136 across lower face 122.

Before proceeding with the mounting of filter paper 134 and outer film layer 138, a short description of ring member 148 follows.

Ring member 148 is cylindrical and has a tapered inner surface 149 and a substantially vertical outer surface 151 each surface extending between upper and lower annular edges 156 and 158. A tapered inner surface 149 mates with tapered wall portion 130 of outer wall 128 of body 92 so that as ring member 148 is slipped over lower face 122 and slid axially along tapered wall portion 130 of body 92, outer film layer 138 is pressed by ring member 148 against inner film layer 136, which in turn is pressed against tapered wall portion 130. Ring member 148 is slid axially inwardly until the movement is stopped by the mating tapers and fall of a locking bead 157 into an annular locking groove formed around the cell body 92. Lower annular edge 158 of ring member 148 has a horizontal flat face spaced inwardly, or upwardly as seen in FIG. 7, from lower rim 126 of body 92. Outer film skirt 142 is positioned over O-ring 146 so that inner and outer film skirts 140 and 142 are spaced apart by O-ring 146. Beyond O-ring 146, both inner and outer film skirts 140 and 142 are again in contact.

Finally, closure sleeve 150, which is cylindrical with opposed upper and lower annular edges 164 and 166 respectively, is slipped over lower face 122 and ring member 148. Sleeve 150 has a vertical inner surface 167 spaced from vertical outer surface 151 forming a vertical separation 169 between them. Annular snap-on bead 168, which extends radially inwardly from sleeve 150 proximate to upper edge 164, snaps into annular groove 170 over both inner and outer film skirts 140 and 142. Bead 168 is spaced from vertical outer surface 151 of ring member 148. During the passage of closure sleeve 150 over vertical wall portion 132 against which it fits tightly, outer and inner film skirts 140 and 142 are drawn away from the lower face 122 so as to tauten both inner and outer film layers 136 and 138 across lower face 122. Once bead 168 snaps into groove 170, inner and outer film layers 136 and 138 are maintained indefinitely in a taut state across lower face 122. An annular flange 172 extends radially inwardly from lower edge 166 of sleeve member 150 at lower edge, or rim, 166. Flange 172 forms an annular inwardly facing stop surface that is spaced axially inwardly from lower rim 126 of ring member 148. The annular stop surface is in a plane that is substantially parallel to the plane of rim 166 and is adapted to be in pressing contact with lower rim 166 so that ring member 148 is aided in being kept in its mounted position around body 12. Annular flange 172 also forms a tapered inner surface that presses film skirts 140 and 142 of films 136 and 138 against the tapered outer surface of tapered portion 130 of outer wall 128 of body 92 in the area of rim 126. Flange 172 includes an annular radially inwardly extending lip 174 that overlaps an annular bevel 176 formed around the outer portion of rim 126 of body 92 and also overlaps films 136 and 138 at bevel 176.

Film support and locking system 144 as described above is a quadruple film support and locking system. The system not only positions inner and outer film layers 136 and 138 tautly across lower face 122, it maintains the two layers indefinitely in the taut position and a seal at the cell window is created. This means that, like holder 10, holder 90 can be preassembled at the factory or at the laboratory by non-technicians, a great saving in cost.

Figure 8:
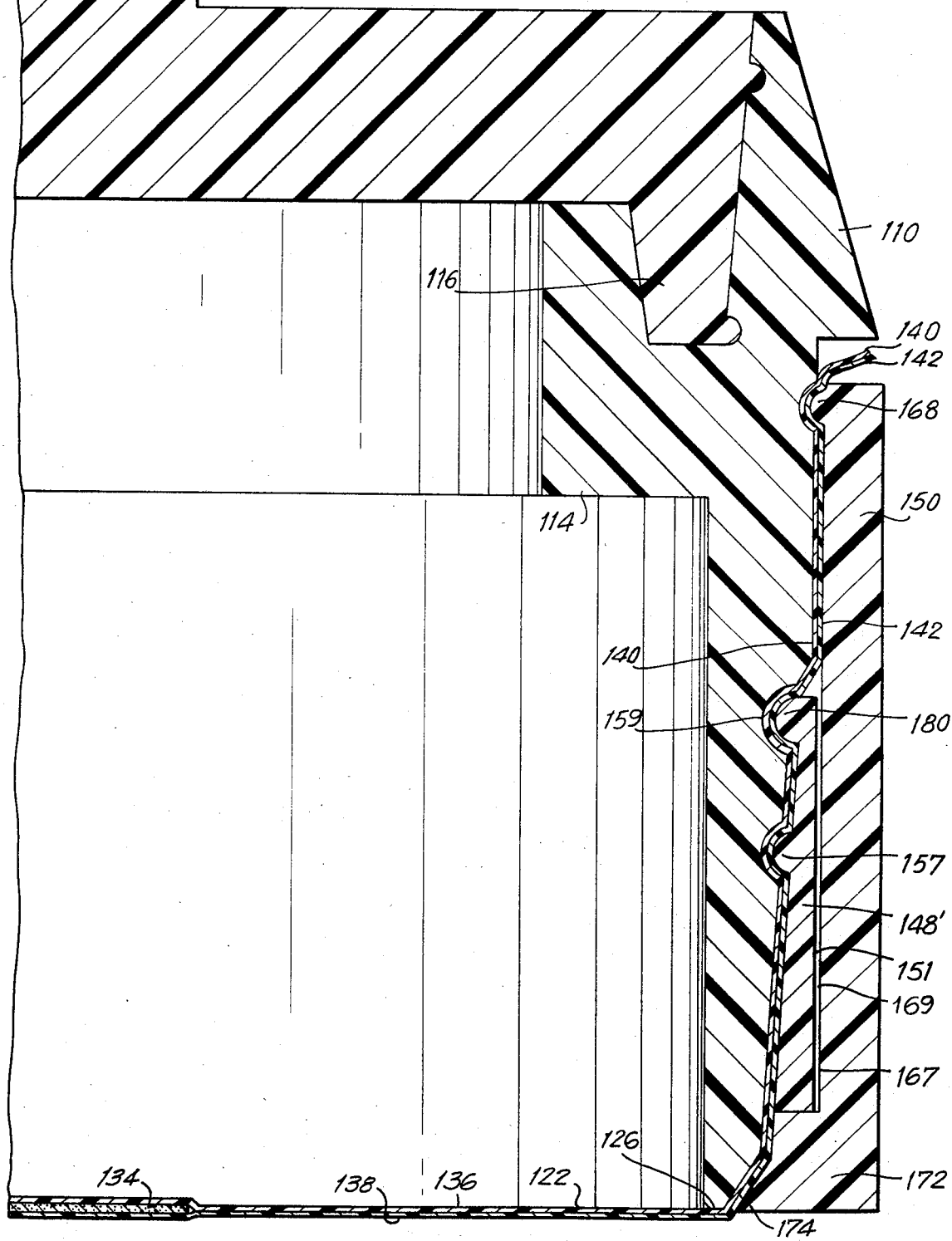
FIG. 8 is an elevational sectional view of the film mounting system having an extended ring member.

An alternative embodiment of the invention particularly relating to ring member 148 as shown in FIG. 7 is shown in FIG. 8. A ring member 148' analogous to ring member 148 of FIG. 7 is shown extending axially inwardly to a second snap mounting connection that includes a circumferential bead 180 that is adapted to snap into circumferential groove 147 originally adapted for the O-ring 146 shown in FIG. 7. The inner surface of ring member 148' is tapered between bead 180 and rim 126, except for bevel 176 at rim 126, to match the outward taper of outer wall 128 of body 92. The outer surface of ring member 148 is vertical and is spaced from vertical inner surface 167 of sleeve member 150. Groove 147 can be changed in dimension from the groove needed for O-ring 146. The remaining features of the system shown in FIG. 8 are as shown in FIG. 7. The embodiment of FIG. 8, however, forms an additional upper gripping area between the upper and lower snap mountings defined by upper and lower beads 180 and 157 and matching grooves 147 and 159. This additional gripping area is a continuation of the lower gripping area between bead 157 and rim 126, so that the upper and lower gripping areas of ring member 148' presses against the double film layers 136 and 138. Ring member 148' can be used with a single film layer as shown in FIGS. 3 and 4.

The particular embodiment shown in FIGS. 1-8 shows a cap that defines a transverse wall that in part defines the cell of the holder. The invention described here can of course be used for sample holders that have a permanent, preformed sealed wall instead of the capped holder described herein.

Figure 7A:
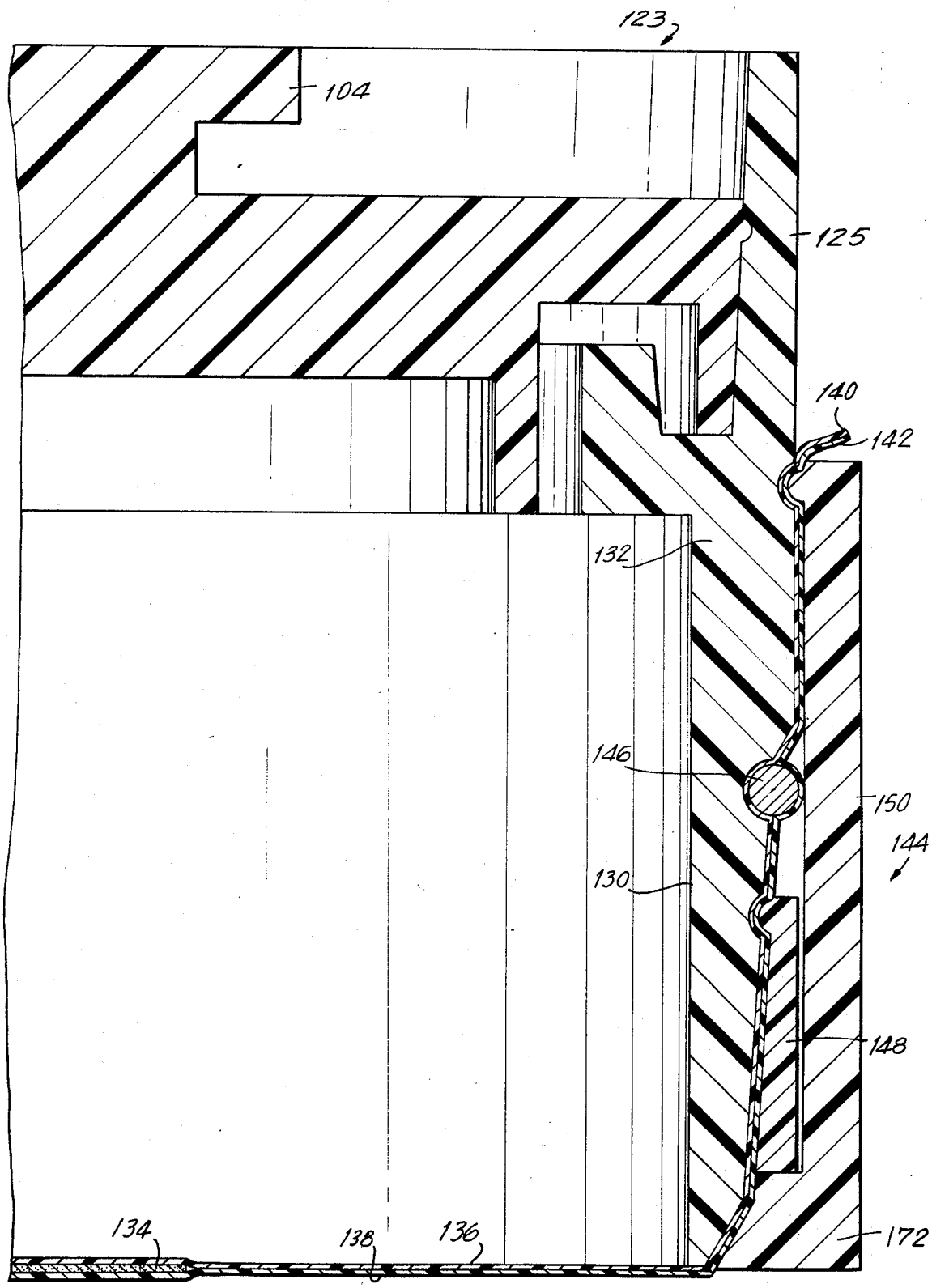
FIG. 7a is an alternate embodiment of the film locking system shown with a removable recessed cap.
Figure 7B:
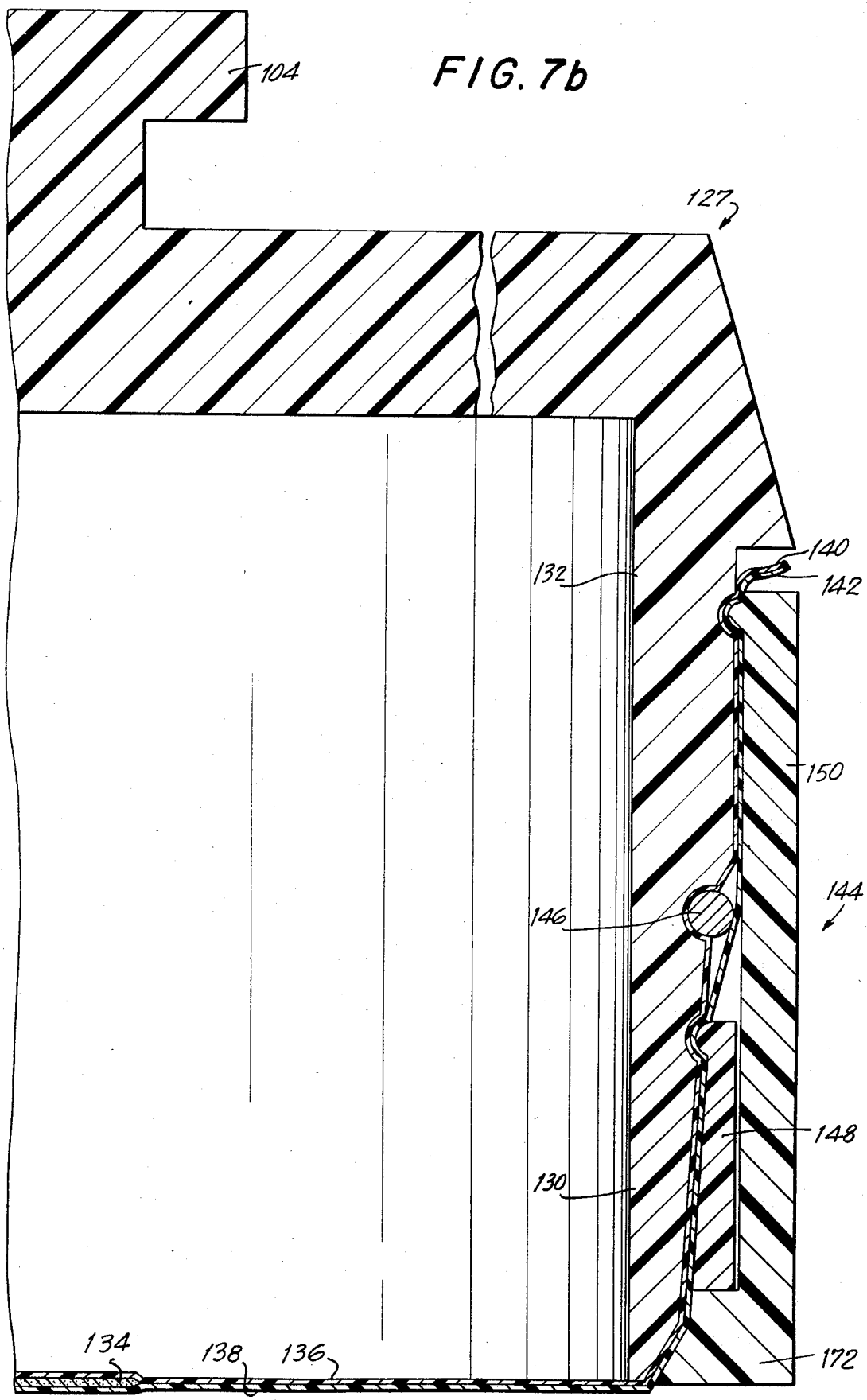
FIG. 7b is an alternate embodiment of the film locking system shown with an integrated cap and holder body with an exposed cap.
Figure 7C:
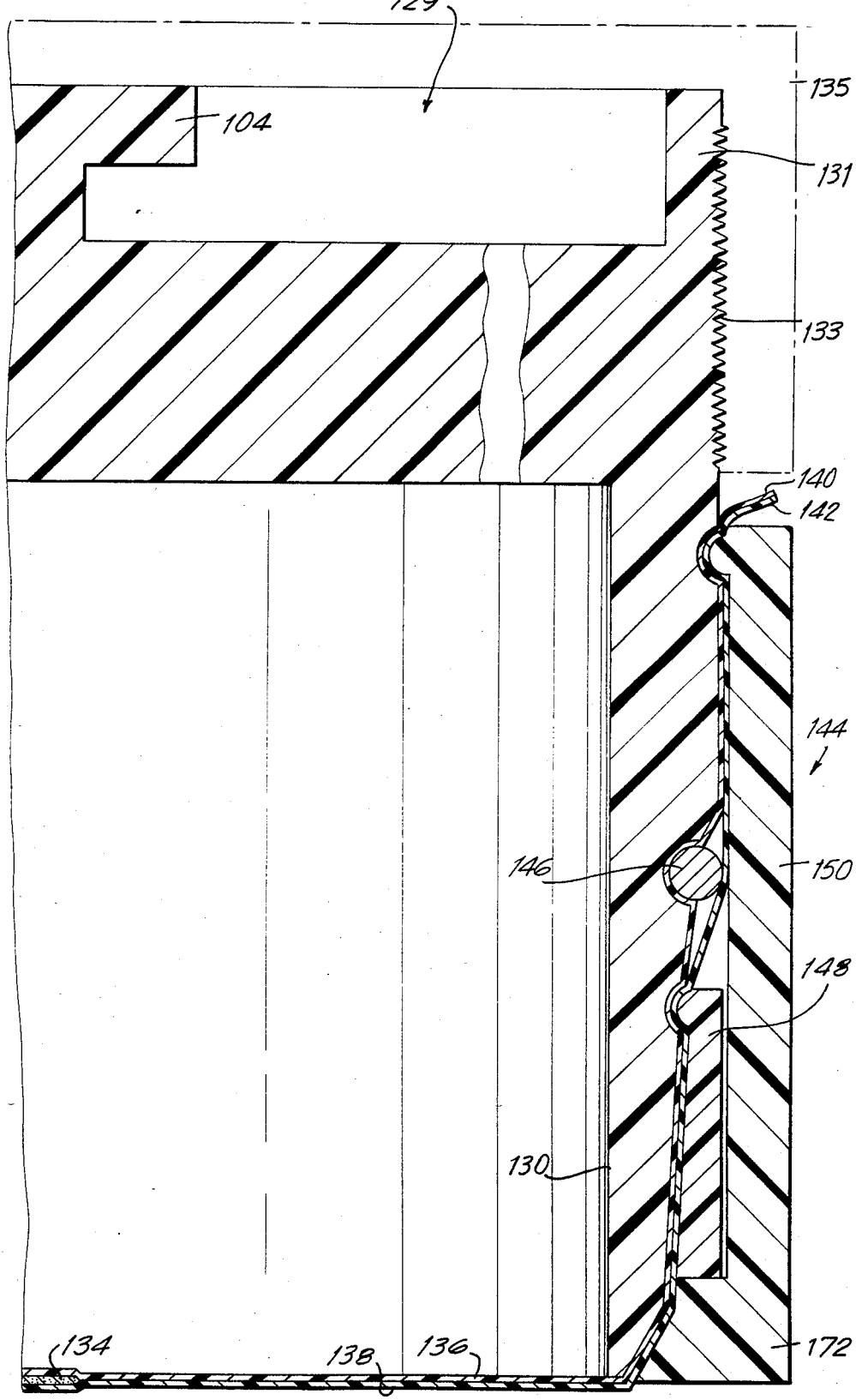
FIG. 7c is an alternate embodiment of the film locking system shown with an integrated cap and holder body with a recessed cap.

Variations on the type of top portion of a typical sample holder are shown in FIGS. 7a, 7b, and 7c. FIG. 7 shows film locking system 144 associated with a removable cap 121 that has its disk top 104 extending above annular rim 124 of the holder body. FIG. 7a illustrates locking system 144 attached to a sample holder body having a removable cap 123 that has its top disk 104 recessed within annular side wall 125 of the holder body. FIG. 7b shows film locking system 144 mounted to a holder body having a top integral cap 127 having its top disk 104 extending exposed above the annular side wall of the holder body. FIG. 7c shows film locking system 144 having a top integral cap 129 recessed within annular side wall 131 of the holder body. The top well formed in part by side wall 131 is provided with external threads 133 adapted to receive the threads of a cylindrical sealing cap 135 shown in phantom lines that can be optionally mounted to the holder body so as to seal the top wall. The various types of top caps shown in FIGS. 7a, 7b, and 7c can be used as well with the single film locking system 52 shown in FIGS. 3 and 4.

As stated previously, the sample holder systems described in FIGS. 1-8 are adapted to hold samples to be analyzed by X-ray spectroscopic analysis. These samples can include powdered or liquid samples. The face of the cell must be substantially leak-proof when the sample is a liquid. The cell of the sample holder systems described are also capable of holding gaseous materials as samples. In such cases, the film across the face of the cell must create a substantially gas-tight volume both at the cap and at the rim of the cell of the holder body.

At this point a step-by-step locking of film to a sample holder is set forth as follows:

(a) placing in an upward disposition an unloaded, substantially cylindrical sample holder body having a substantially cylindrical wall forming a cell, said wall having an outward taper extending from the upper rim of the wall downwardly for a portion of the wall;

(b) positioning a single layer of very thin transparent plastic film across the open cell face;

(c) drawing the skirts of the film around the outer annular walls of the sample holder;

(d) gently sliding a flexible, thin-walled cylindrical ring member tapered to match the taper of the tapered wall portion of the sample holder body around the skirt of the film and the sample holder body;

(e) gently sliding the ring member, which has a circumferential bead at its leading edge, along the tapered wall of the holder body and over the film skirt and forcing the flexible ring member to expand lightly;

(f) gently drawing the film inwardly from the face of the sample holder along the annular wall of the sample holder and so drawing the film tautly across the face of the film body;

(g) positioning the bead of the ring member over the first circumferential locking groove formed in the outer annular wall of the holder body and locking the ring member and the film skirt to the annular wall by allowing the annular bead to contract and fall into the locking groove of the annular wall of the holder body;

(h) passing the sleeve member leading with its circumferential bead over the face and annular wall of the holder body and over the ring member with the inner surface of the sleeve member spaced slightly outwardly from the outer surface of the ring member;

(i) pressing the skirt of the film to the vertical portion of the annular wall of the holder body past the tapered portion of the annular wall and drawing the film skirt more tautly around the annular wall of the holder body;

(j) positioning the bead of the sleeve member over the second matching locking groove formed in the annular wall of the holder body and locking the sleeve member and the film skirt to the holder body by allowing the bead of the sleeve member to fall into the matching second groove formed in the annular outer wall of the holder body; and simultaneously both pressing the annular inner surface of the inwardly extending flange of the sleeve member against the film layer that extends axially inwardly from the face of the holder body along a portion of annular outer wall to the ring member, and also further locking the ring member to its mounted position around the holder body.

The cell of the holder body can then be filled with the sample substance, which can be in powder, liquid, or gas form.

When a locking O-ring is desired, a step is added between steps (c) and (d) above, namely, the step of sliding a flexible O-ring over the annular outer wall of the holder body and pressing the film skirt to the holder body and drawing the film tautly across the face of the holder body.

When a piece of filter paper impregnated with a liquid sample to be analyzed positioned at the center of the face of the sample holder, two layers of film are used to sandwich the filter paper. Here, an O-ring must be used. Instead of steps (b) and (c) above, substitute the following steps:

(1) positioning a first inner layer of very thin transparent plastic film across the open cell face;

(2) placing the impregnated filter paper on the first layer of film at the center of the cell face;

(3) positioning a second inner layer of very thin transparent plastic film across the cell face over the first layer of film and the filter paper so as to sandwich the filter paper between the two film layers;

(4) drawing the skirts of the first and second film layers around the annular outer wall of the sample holder;

(5) sliding a flexible O-ring over the annular outer wall of the holder body and pressing the first film skirt to the holder body and drawing the first film layer tautly across the face of the holder body;

(6) passing the second film skirt over the O-ring.

In steps (d), (e), (f), (g), (h), (i), and (j) as set forth above, substitute the first and second film layers above for the single film layer and film skirt.

Figure 9:
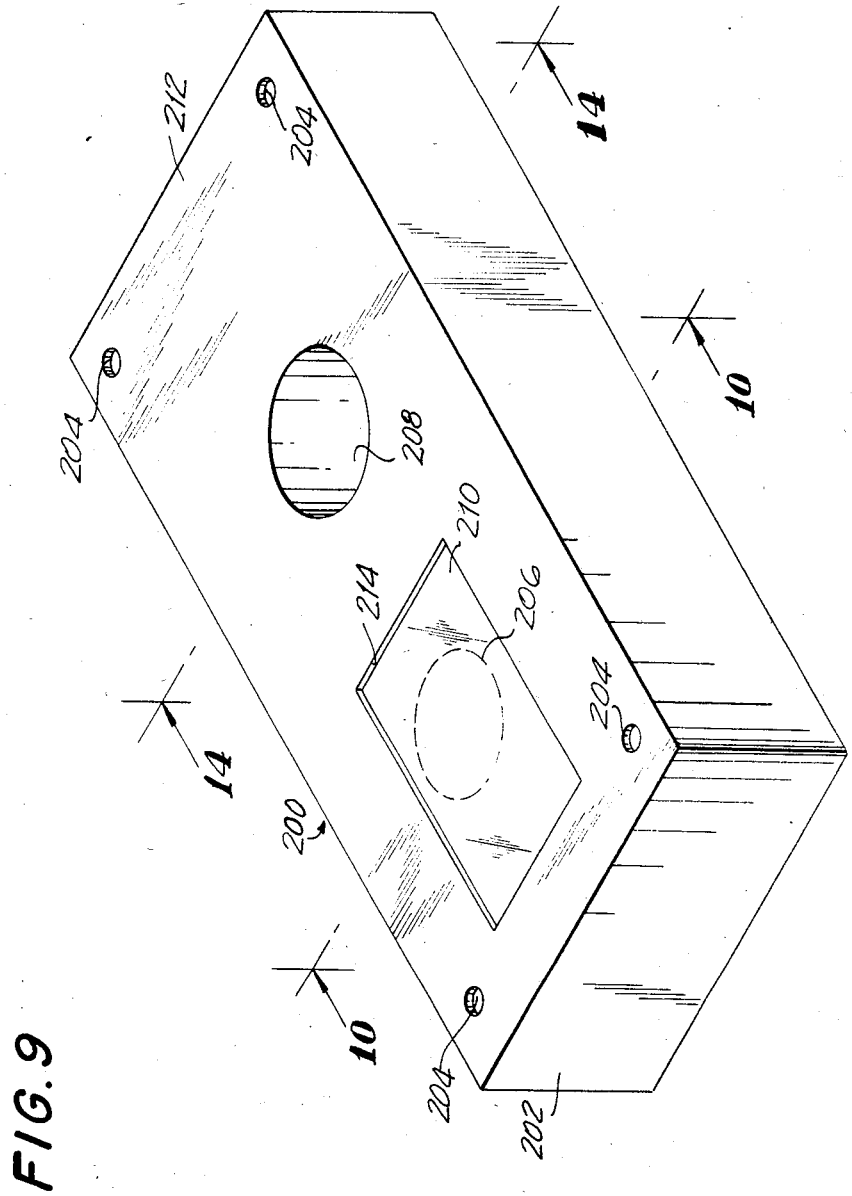
FIG. 9 is an assembly block for sample holder film assembly.
Figure 10:
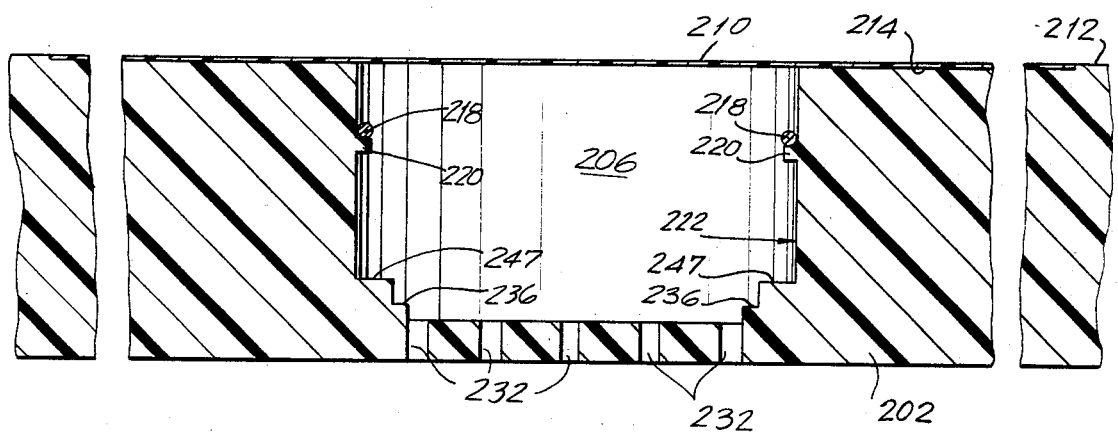
FIG. 10 is an elevational cross-section of assembly block at first well.
Figure 11:
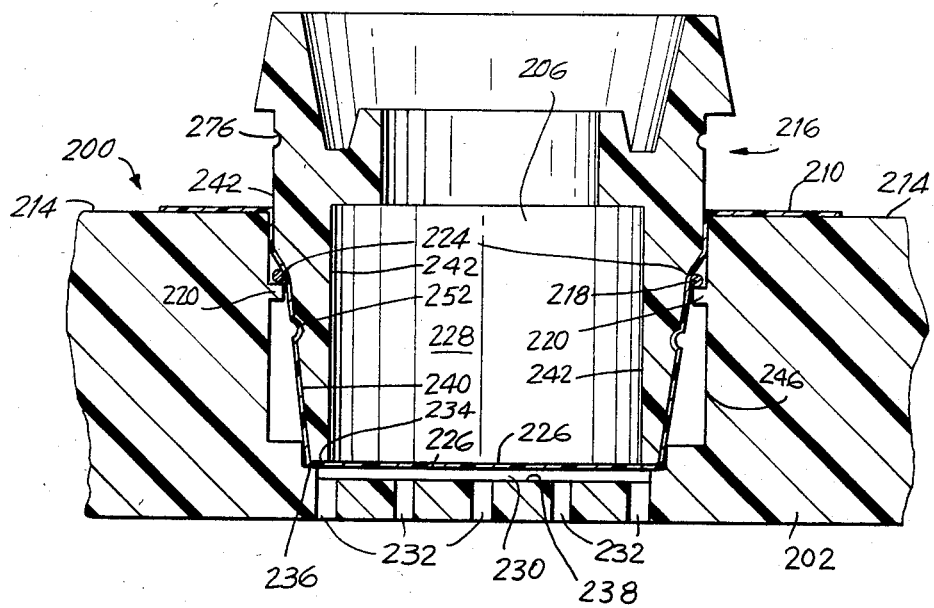
FIG. 11 is a sectional view of first well with inner body inserted and assembled to O-ring and film.

In accordance with the present invention, a film assembly system 200 shown in FIG. 9 is used to mount the film to the cell face of the holder body. Assembly system 200 includes a substantially quadrilateral assembly block 202 with four screw holes 204 at its top four corners for securing the block to a base structure (not shown). First and second substantially cylindrical wells 206 and 208 are formed in block 202, spaced apart and extending generally vertically in the block. An elevational section of block 202 taken through first well 206 is shown in FIG. 10. A layer of film 210 is shown horizontally positioned over first well 206 in FIGS. 9 and 10. Film 210 is shown as rectangular but it can be circular. The horizontal top surface 212 of block 202 forms a horizontal film recess 214 around first well 206 adapted to position film 210. As shown in FIG. 11, a substantially cylindrical sample holder body 216 analogous to the holder bodies 12 and 92 shown in FIGS. 1-8 has been pressed downwardly into first well 206 so as to secure film 210 to the outer wall of holder body 216 with an optional O-ring 218 that has been set around a horizontal, annular shoulder 220 spaced slightly below top surface 212 and extending radially inwardly from the vertical side surface 222 of first well 206. O-ring 218 extends radially inwardly into well 206 past the inward extension of shoulder 220 so as to allow the O-ring access to O-ring groove 224 and to prevent shoulder 220 from striking inner tapered surface 240 of body 216 during the insertion process. As seen in FIG. 11, O-ring 218 has been snapped into circumferential groove 224 formed in the outer wall of body 216 along with film 210, which is pressed into groove 224 by the O-ring. Film 210 is drawn tautly across face 216 of cell 228 of body 216 during the descent of body 216 into well 206. A horizontal space 230 is formed beneath face 216 under film 210 so as to allow trapped air free access to a plurality of vertical air passages 230 formed through the bottom wall of block 202 to the atmosphere. The annular rim 234 defining face 226 of cell 228 is set upon a bottom horizontal annular shoulder 236 having a horizontal bearing surface that is positioned just above and around horizontal bottom surface 238 of first well 206. As shown in FIG. 11, the top portion of body 216 extends well above top surface 212 of block 202 so as to allow easy access for an assembler to handle holder body 216 during its insertion into well 206 and its removal from the well. Film layer 210 has been drawn from its position in film recess 214 over rim 234 and face 226 of body 216; drawn past O-ring 218, which is snapped into groove 220 after the tapered surface 240 of holder body has passed past the O-ring; and drawn past the vertical surface 242 of the holder body, leaving a tailing of skirt 210 still remaining in film recess 214. It is noted that film 210 is being run between the inner tapered surface 240 of body 216 and O-ring 218 during the insertion of body 216 into well 206 so that a certain pulling of film 210 across face 226 is accomplished. The insertion of body 216 is done gently to avoid any rupturing of the film. When rim 234 of body 216 reaches bottom shoulder 236, O-ring 218 snaps into groove 224 with film 210 circumferentially pressed into a locking mode in the groove under the O-ring. Body 216 is then lifted from well 206 and the skirt of film 210 is gently pulled to eliminate any irregularities, if necessary.

Figure 12:
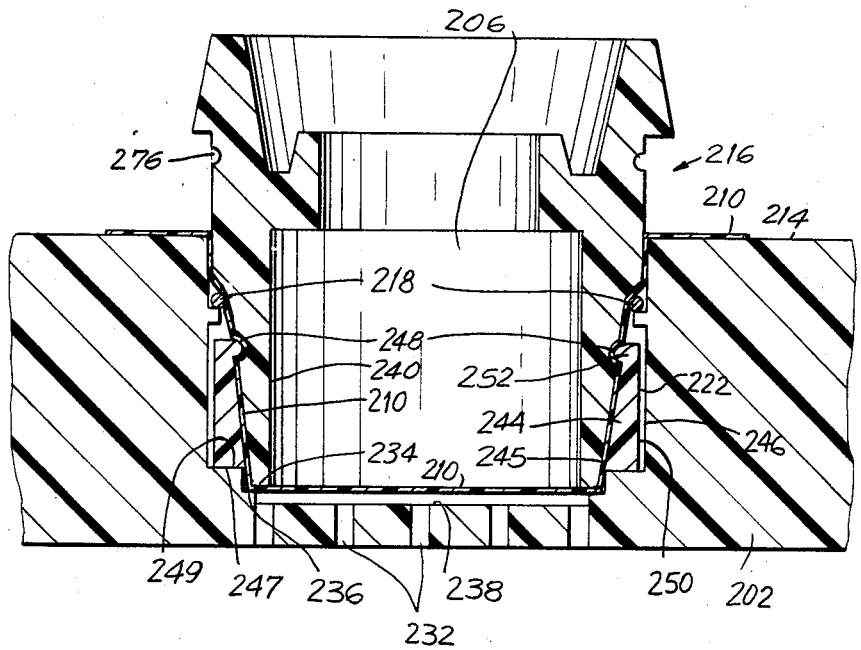
FIG. 12 is a sectional view of first well with inner body inserted and assembled to film ring and film.

FIG. 12 illustrates holder body 12 inserted into first well 206. In the interim between FIG. 11 and FIG. 12, the assembler has removed holder body 216 from first well 206 and placed a ring member 244 analogous to ring members 54 and 148 of FIGS. 1-7. Ring member 244 includes a tapered inner surface 245 adapted to fit over tapered outer surface 240 of holder body 216 and a vertical outer surface 246 spaced slightly from vertical inner surface 222 of first well 206. Ring member 244 is made of the same material as ring members 54 and 148 described previously.

Figure 13:
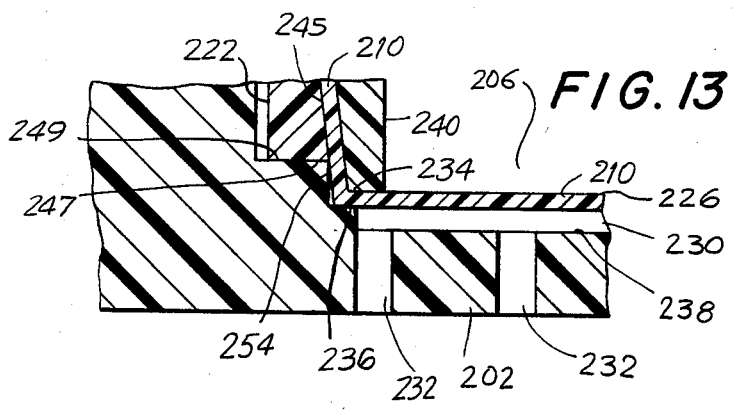
FIG. 13 is a detailed view of film positioning portion of FIG. 12.

As best seen in FIG. 13, a horizontal annular shoulder 247 is positioned above and radially outwardly from annular bottom shoulder 236 extends around the bottom portion of first well 206. When the assembler places ring member 244 into well 206, the ring member is slid downwards until its flared bottom rim 249 is set against shoulder 247. Again, the top portion of body 216 extends well above the top of assembly block 202 so as to give the film assembler easy gripping access to the body during its placement into first well 206. As body 216 is gently pressed downwards, tapered outer surface 240 of body 216 slides over a snap-in bead 248 extending radially inwardly from the top, or axially inward of end of ring member 244. During this downward movement, flexible ring member 244 is pressed into the vertical recess 250 formed between vertical side surface 222 of well 206 and vertical side surface 246 of ring member 244.

As the gentle downward movement continues, film 210 is further tensioned across face 226 by the pulling pressure on the film between bead 248 and tapered surface 240 of body 216 and the pulling pressure between tapered surfaces 245 and 240 of the ring member 244 and body 216. A second circumferential groove 252 is formed around body 216 at outer tapered surface 240 downward from the first, or O-ring, groove 224. Groove 252 is adapted to receive bead 248 of ring member 244, so that when bead 248 reaches groove 252, bead 248 snaps into groove 252 thus locking ring member 244 to holder body 216 and locking film 210 between tapered surfaces 245 and 240 and into groove 252 by bead 248. Simultaneous with the snap-in of bead 248 into groove 252, rim 234 of body 216 presses against bottom shoulder 236 of block 202. Air trapped between film 210 and bottom surface 238 is passed through air passages 232 to the atmosphere. The assembler then lifts body 216 with its partially mounted film 210 and mounted ring member 244 and O-ring 218 from first well 206. The assembler then inspects the film and will gently remove any irregularities in the position of the film.

FIG. 13 illustrates in detail the position of film 210 between tapered surface 245 of ring member 245 and tapered surface 240 of body 216 at shoulder 247 and the position of film 210 at face 226 between rim 234 of body 216 and bottom shoulder 236. Both rim 234 and bottom shoulder 236 are slightly rounded at their corners between tapered surface 240 of body 216 and matching tapered surface 254 of block 202 that extends upwardly from shoulder 236.

It is noted at this point that upon removal of the partially assembled sample holder from well 206 after the assembly process described relating to FIG. 12, tailings of film 210 will dangle from the area of O-ring 218.

If optional O-ring 218 is not mounted, then the steps relating to mounting the film under the O-ring are not taken and only the steps beginning with mounting the film under ring member 244 are taken.

Figure 14:
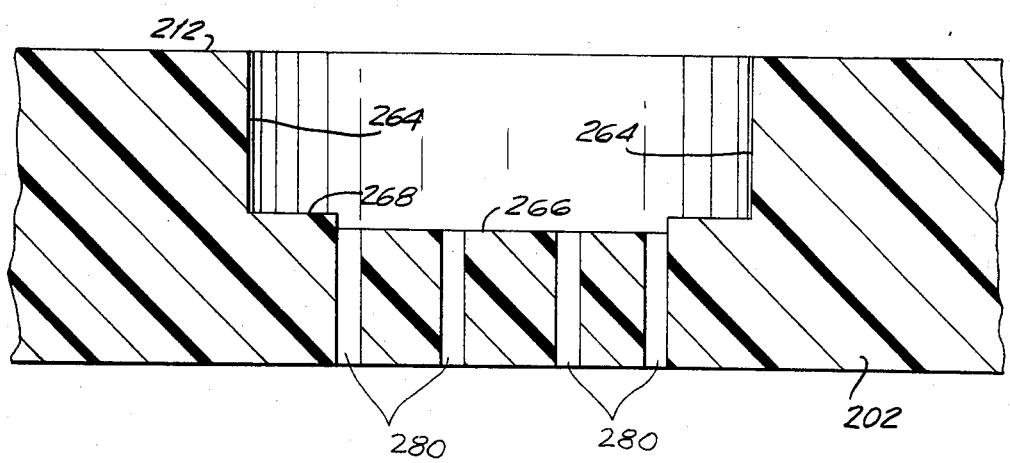
FIG. 14 is an elevational cross-section of assembly block at second well.
Figure 15:
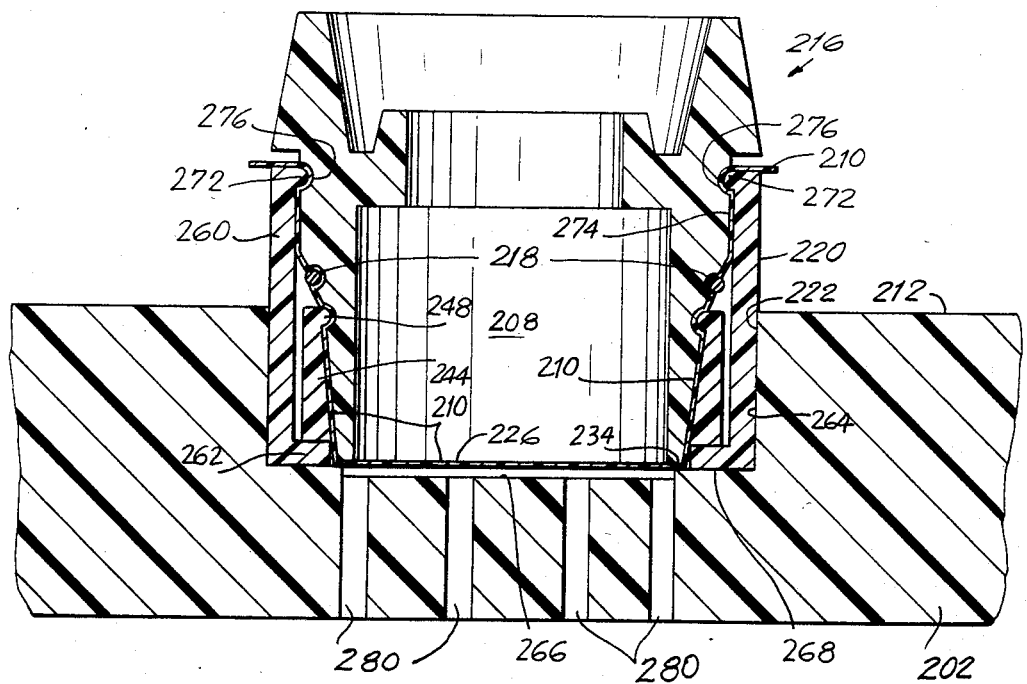
FIG. 15 is a sectional view of second well with partially assembled inner body, film, and film ring inserted into sleeve member for final film assembly.

FIG. 14 is an elevational cross-section of second well 208 in assembly block 202. FIG. 15 illustrates the partially assembled holder body 216, film ring 244 and film 210 having been inserted into second well 208 to complete the third and final stage of the film assembly process.

Prior to the insertion of the partially assembled holder into well 208, the assembler has inserted a substantially cylindrical sleeve member 260, which is analogous to sleeve members 56 and 150 of FIGS. 1-7. Sleeve member 260 includes a lower annular flange 262 that extends radially inwardly from the bottom portion of sleeve 260. Second well 208 is partially defined by a vertical annular side surface 264, a horizontal bottom surface 266, and an annular shoulder 268 having a horizontal top surface located at the intersection of bottom surface 266 and side surface 264. Annular outer surface 270 of sleeve 260 is fit against annular side surface 264 of well 208 and the bottom surface of flange 262 lies upon annular shoulder 268.

Body 216 is then slid downwards into well 208 and in particular into the cylindrical volume formed by sleeve 260 in well 208. Sleeve 260 includes annular bead 272, which extends radially inwardly from the side walls of the sleeve. The tailing of film 210 mentioned earlier is kept from doubling over during the insertion and final film mounting process so that bead 272 presses film 210 against vertical surface portion 274 of body 216. The insertion process continues until rim 234 of body 216 strikes annular shoulder 268 and bead 272 simultaneously snaps into annular groove 276 and bead 272 pressing film 210 into groove 276 thus completing the film mounting process. An air pocket 278 is defined by film 210 across face 280 at lower rim 282. Air trapped under face 280 escapes through a number of preferably vertical air passages 284 formed in block 202 between bottom surface 266 and the bottom outer surface of the block. At this point, the assembler removes the film assembled unit from second well 208 for use or for packing for shipment.

Assembly block system 200 enables even an unskilled worker to easily and quickly mount film to a sample holder body. The mounting elements present in assembly block 202 are particularly adapted to enable the assembler to gently slip on and lock the film to the holder with an evenness of distribution of mounting and locking forces that enable the film to be set into position with little possibility of tearing or ripping of the film.

It will be appreciated that the film assembly process described above as relating to both the film assembly without assembly block 202 and with assembly block 202 results in the film being locked to the sample holder body by the four locking pressures described earlier as relating to FIGS. 1-7 and described in detail with regard to FIGS. 1-4. O-ring 218 as noted previously is an optional locking system and is only needed when two film layers are needed. When two layers of film are needed, the first film layer is mounted to body 216 as described in relation to the mounting of O-ring 218 in first well 206. Upon removal of body 216 from well 206, the second film is set into film recess 214 and ring member 244 is likewise set into first well 206 as described. The film mounting process then continues as described above.

Mounting block 202 described above can be easily modified to enable the assembler or a technician to remove a locking cap from a sample holder containing a sample that has been analyzed. Although it is common to discard the sample holder with the analyzed sample after X-ray analysis, recovery of the analyzed sample is sometimes desired. It can be appreciated that the removal of the cap by one hand while holding the holder body with the other and pulling the cap from a snap-in connection with the body can be awkward, and in the case of certain samples, such as noxious materials, even dangerous.

Figure 16:
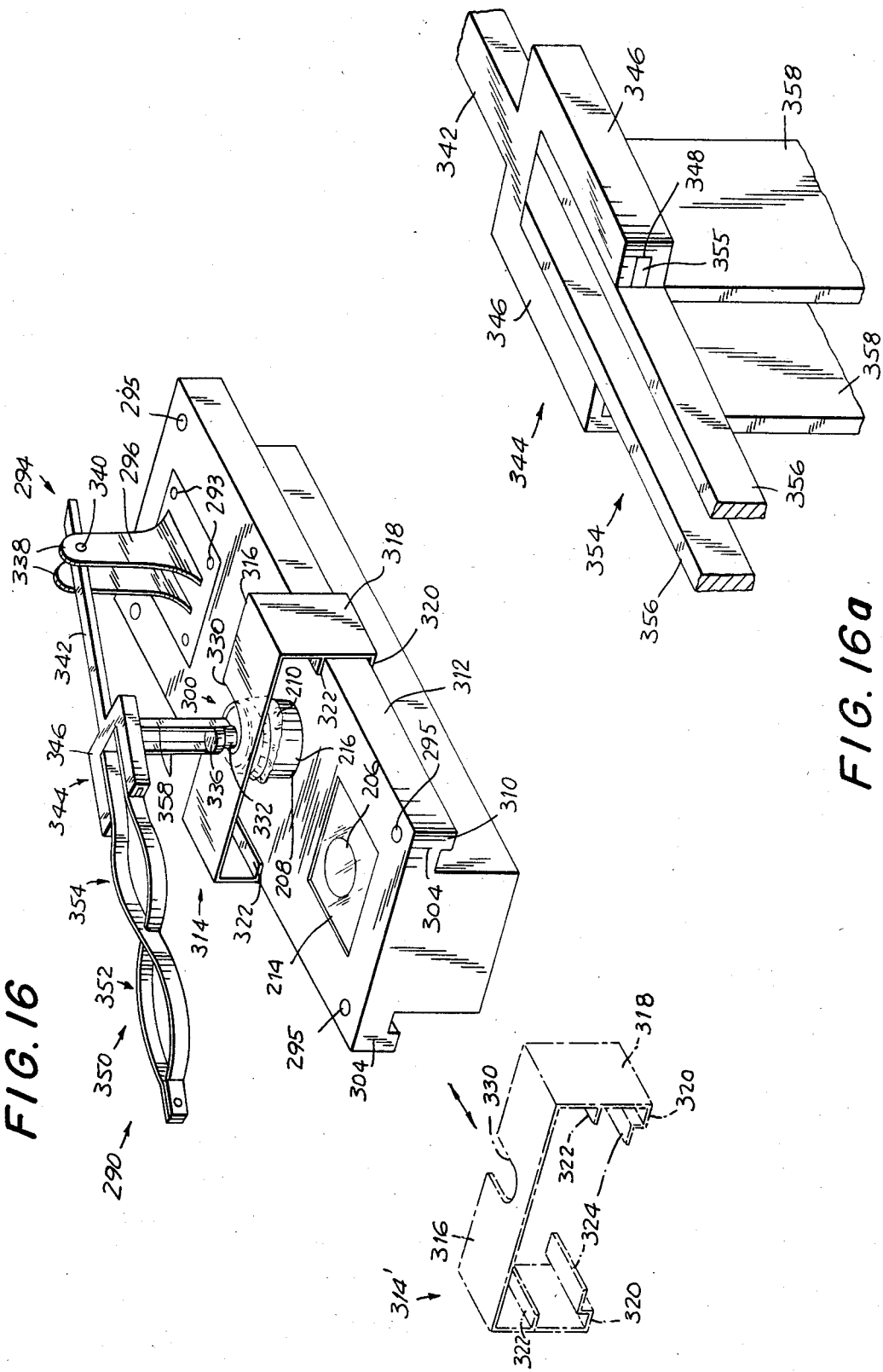
FIG. 16 is a cap removal system.
Figure 17:
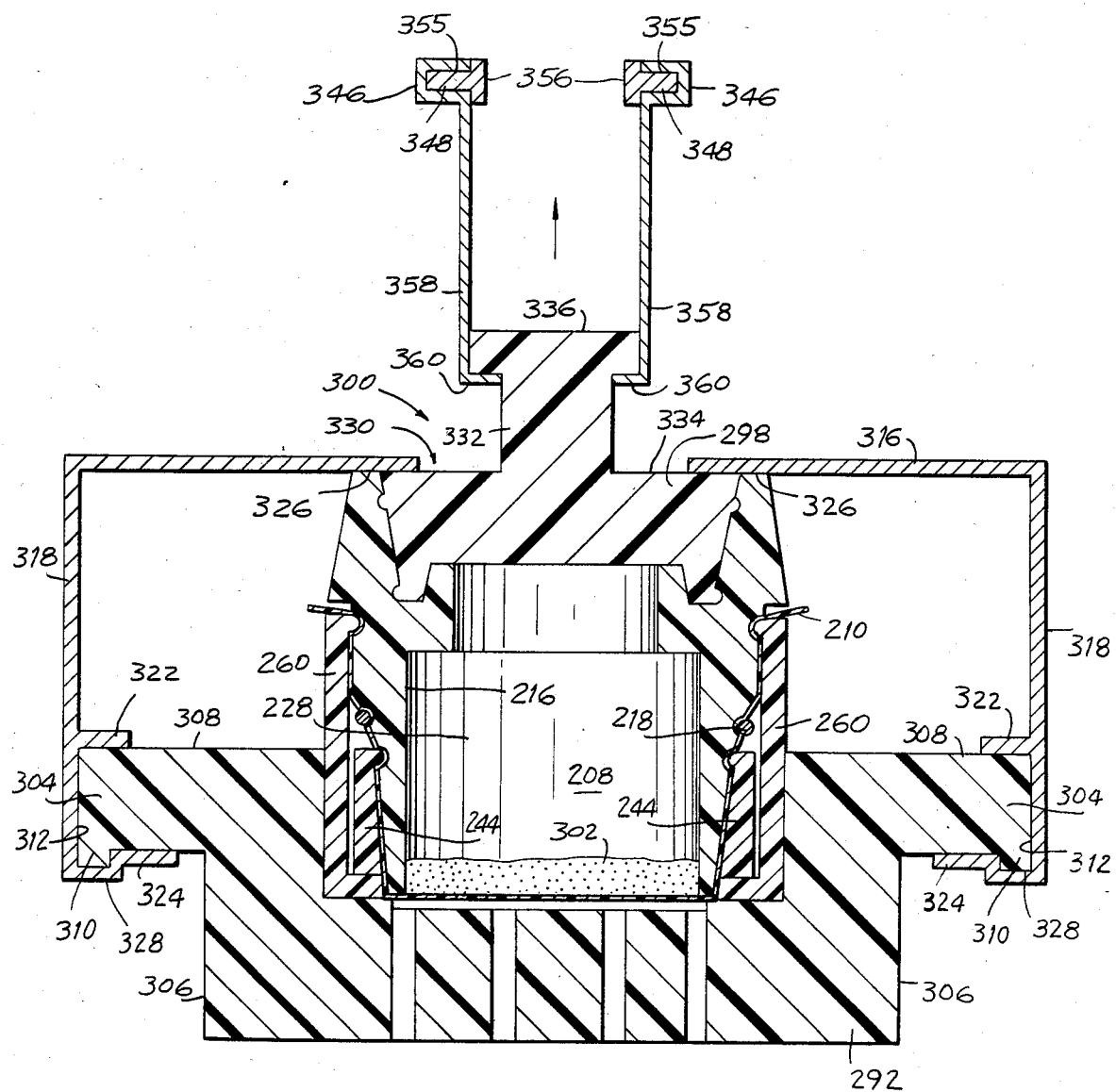
FIG. 17 is a sectional view of second well with loaded sample holder in place for cap removal.

A cap removal system 290 utilizing second well 208 previously described is shown in FIGS. 16, 16a, and 17. A block 292 made of any suitable rigid material, forms a pair of vertical, substantially cylindrical mounting wells, which will be designated here as first and second wells 206 and 208 as for the two wells of block 202 above. Block 292 is used for film assembly and is similar to block 202 but is slightly longer dimension than block 202 to accommodate a lifting apparatus 294 having a base 296 that is positioned sufficiently spaced from well 208 so as to obtain a lifting leverage between base 296 and well 208 as will be described. Base 296 is suitably secured to the top of block 292 by screws 293. Block 292 is suitably mounted to a support structure (not shown) by screws 295.

A sample holder 300 has been set into well 208 of block 292. Sample holder 300 includes a removable cap 298 that has been snap-mounted to the top of the holder body, designated here as sample holder body 216 as described above.

Cell 228 of body 216 contains a powdered sample 302 that has been analyzed lying against film 210 at face 226 located at rim 234. First well 206 is seen in FIG. 16 near second well 208 positioned opposite from base 296 relative to second well 208. Sample holder 300 is still mounted with film 210 secured to body 216 by O-ring 218, ring member 244, and sleeve member 260.

Block 292 is provided with a pair of opposed elongated locking flanges 304 extending outwardly from the upper portions of the longitudinal vertical side walls 306 of block 292. The horizontal top wall 308 of block 292 extends outwardly from side walls 306 to form the top walls of locking flanges 304, which also include parallel elongated locking tabs, or keys, 310 which extend downwardly from the horizontal bottom walls of flanges 304 at the outer side walls 312 of the flanges. Locking flanges 304 extend longitudinally along block 292 on opposite sides of wells 206 and 208 and lifting apparatus 294.

A slidable hold-down member 314 is adapted to be slid onto and along locking flanges 304 to a position over second well 308 and cap 298 of sample holder 300. Hold down member 314 is also shown in phantom lines spaced away from block 292 and designated as 314'. Hold down member 314 comprises a rectangular flat top plate 316, a pair of opposed vertical side plates 318 connected to the sides of top plate 316, and an opposed pair of longitudinally disposed side tracks 320 that are adapted to mount hold-down member to block 292 over locking flanges 304 and to slidably pass hold-down member 314 along locking flanges 304 to a position over cap 298 in a manner to be explained. Each side track 320 is defined by a pair of upper and lower opposed elongated flat ribs 322 and 324 and outer side wall 318 connected to ribs 322 and 324. Ribs 322 and 324 are adapted to slidably mount over and under flange top and bottom walls 308 and 310 respectively. As seen most clearly in FIG. 17, side plates 318 extend vertically upwardly over upper ribs 322 so as to position top plate 316 to a vertical blocking relationship to the top of upper rim 326 of holder body 216. Top plate 316 is spaced from upper rib 322 and, to a slighter greater extent, from top wall 308 of block 292. Key ways 328 extend vertically downwards from the outer sides of lower ribs 324 in sliding relationship with keys 310 of block 292 in order to give a better grip of hold-down member 314 with locking flanges 304 of the block. A cutout 330 preferably hemispherical in configuration as seen in FIG. 16 is formed by top plate 316 with an opening on the forward side of top plate 316 so that, as hold-down member 314 is slid forward on block 292 from its position near first well 206 to its position over second well 208, cutout 330 accepts cylindrical post 332 of cap 298 that extends vertically upwards from horizontal top wall 334 of cap 298, which in turn is generally level with top run 326 of holder body 216. A cylindrical gripping disk 336 is mounted to the top of post 332. Cutout 330 is formed so as to position top plate 316 out of vertical alignment with any part of cap 298, particularly top wall 334 but at the same time leaving top plate 316 in vertical alignment, preferably in touching contact, with upper rim 326 of holder body 216.

When the X-ray analysis of powdered sample 302 has been completed and it is considered desirable to remove cap 298 so as to gain access to the sample, sample holder 300 is placed in second well 208, with a portion of holder body 216 set in the well and cap 298 extending above the well as shown in FIG. 17. Hold down member 314 is fitted onto block 292 and moved from its non-mounted position at 314' to its mounted position at 314.

Lifting apparatus 294 is provided with a spaced pair of mounting columns 338 extending vertically from base 296 and a horizontal pin 340 extending transversely in relationship to block 292 and laterally to hold-down member 314. Pin 340, as is base 296 and second well 208, is generally centrally located with respect to side walls 306 of block 292. An arm 342 is rotatably connected at one end to pin 340 and extends over the longitudinal center portion of block 292 to a fork portion 344 that is disposed over second well 208. The two prongs 346, which open towards first well 206, form facing recesses 348 as seen in FIG. 16a. As seen best in FIG. 16, a gripper 350 having a handle portion 352 and an inwardly biased gripping portion 354 has a pair of opposed wings 355 extending outwardly from each of the two inwardly biased gripping arms 356 of gripping portion 354. Wings 355 are adapted to be slidingly and removably received by recesses 348 of prongs 346. A pair of elongated clamp members 358 extend downwardly from the ends of gripping arms 356 to a pair of inwardly facing jaws, or grips, 360 that are adapted to enclose a portion of cylindrical post 332 and to press under the lower surface of gripping disk 336.

In operation, wings 355 of gripper 350 are slid into recesses 348 of prongs 346. Simultaneously with the mounting of gripper 350 with prongs 346, jaws 360 are slid under disk 336 and around post 332 of cap 298. Prongs 346 are biased outwardly apart but movement stopped at prongs 346 so that jaws 360 remain in lifting relationship with disk 336. The operator then lifts handle portion 352 so that arm 342 rotates about pin 340 and clamp members 358 and jaws 360 are raised upwardly so that jaws 360 pull disk 336 upwardly and so pull cap 298 free from its engagement at upper and lower snap-in connections 301 and 303 with holder body 216. That is, top plate 316 engages upper rim 326 of holder body 216 at the periphery of cutout 330 so that holder body 216 is pressed into remaining in its position in well 208. The restraining pressure is concentrated between lower ribs 324 of hold-down member 314 and flange bottom wall 310 of locking flange 304.

After removal of the cap, the cap is slid from between jaws 360 and gripper 350 is slid out of its connection to prongs 346 by withdrawal of wings 355 from recesses 348. Holder body 216 is then ready for lifting by the operator with or without a tool from well 208 for recovery of sample 302.

The step-by-step operation of the mounting of film to the sample holder body by use of film assembly system 200 without an O-ring is as follows:

(a) placing a cylindrical ring member into the first well and setting the bottom rim of the ring member on the annular ring shoulder in the first well;

(b) placing a single layer sheet of transparent plastic film in the film recess around the first well of the assembly block;

(c) inserting a sample holder body bottom rim downwards into the first well against the sheet of film and pressing the body and the film into the first well and tautening the film across the face of the bottom rim of the holder body;

(d) snapping the annular ring slot in the sample holder body into connection with the annular bead of the ring member so that the ring member is connected to the holder body, the skirt of the film is pressed against the outer surface of the holder body by the ring member and by the bead of the ring member;

(e) removing the holder body with the partially secured mounted film with the ring member from the first well by holding the portion of the holder body extending above the top surface of the assembly block;

(f) placing a cylindrical sleeve member into the second well of the assembly block against the annular sleeve shoulder in the second well;

(g) inserting the holder body with the partially secured film and ring member film face downwards into the second well so that the upper and lower portions press the skirt of the film against the outer surface of the holder body above and below the ring member and further tautening the film across the face of the holder;

(h) snapping the annular sleeve slot in the sample holder body into connection with the annular bead of the sleeve member so that the sleeve member is connected to the holder body, the skirt of the film is pressed against the outer surface of the holder body by the sleeve member and by the bead of the sleeve member; and (i) removing the holder body with the fully secured mounted film with the ring member and the sleeve member from the second well by holding the portion of the holder body extending above the top surface of the assembly block.

When an O-ring is also to be mounted to the holder body, for step (a) above, substitute the following step:

(1) placing an O-ring into the first well and setting the O-ring on the annular O-ring shoulder in the first well;

between steps (b) and (c) above insert the following steps:

(2) inserting the sample holder body bottom rim downwards into the first well against the sheet of film and pressing the holder body and the film into the first well and tautening the film across the face of the bottom rim of the holder body;

(3) removing the holder body with the partially secured mounted film with the O-ring from the first well by holding the portion of the holder body extending above the top surface of the assembly block; and (4) add step (a).

Two film sheets can be mounted to the sample holder body as follows:

change step (b) to read (b') placing a second single layer sheet of transparent plastic film in the film recess around the first well of the assembly block.

The embodiments of the invention particularly disclosed here are presented merely as examples of the invention. Other embodiments, forms, and modifications of the invention coming within the proper scope of the appended claims will, of course, readily suggest themselves to those skilled in the art.

What is claimed is:

1. A film handling, positioning, and locking system for a vented or closed disposable sample holder for sample materials for spectroscopic fluorescence analysis, comprising, in combination:

a substantially cylindrical body having a substantially annular wall forming a cell adapted to contain said sample material, said wall having a rim portion defining an open face of said cell, film means positioned across said face of said cell for sealing said face and preventing the passage of said sample material from said cell and for maintaining a taut surface for said sample material for the sample analysis, said film means including a film skirt for engagement with said annular wall of said body, flexible ring means positioned around a first portion of said annular wall of said body associated with said face, said flexible ring means being for pressing said film skirt to said first portion and for maintaining said film means across said face sufficient to maintain a taut surface of said film means across said face without imposition of undue strain upon the film, and sleeve means positioned around said annular wall of said body and said ring means and closely spaced radially from said ring means, said sleeve means being for pressing said film skirt to second and third portions of said annular wall spaced axially outwardly and inwardly respectively from said first portion of said annular wall; for holding said ring means from moving axially from its position around said annular wall of said holder body; and for maintaining the taut surface of said film means across said face of said cell.

2. A system according to claim 1, wherein said first portion of said annular wall is located spaced inwardly from said face of said cell.

3. A system according to claim 2, wherein said third portion of said annular wall is located between said face of said cell and said first portion of said annular wall.

4. A system according to claim 3, wherein said film means includes a single film layer and said skirt portion means includes a single film skirt layer.

5. A system according to claim 3, further including an O-ring means snap mounted to said annular wall of said body between said first and second portions of said annular wall spaced axially inwardly from said sleeve means, said O-ring means being for pressing said film skirt portion to said annular wall and for maintaining said film means taut across said face.

6. A system according to claim 5, wherein said sample material is impregnated in a filter paper positioned at the center of said face of said cell, and said film means includes a first film layer positioned inwardly of said filter paper relative to said cell and a second film layer positioned outwardly of said filter, said first film layer including a first film skirt positioned between said ring means and said first portion of annular wall of said body, between said O-ring means and said annular wall, and between said sleeve means and said second and third portions of said annular wall; and said second film layer includes a second film skirt layer positioned between said first skirt portion and said first portion of said film ring, between said O-ring and said sleeve means, and between said sleeve means and said second and third portions of annular wall.

7. A system according to claim 5, further including means for limiting the movement of said ring means in an axial direction inwardly from said face.

8. A system according to claim 7, further including means for removably connecting said ring means with said body.

9. A system according to claim 8, further including means for removably connecting said sleeve means with said body.

10. A system according to claim 9, wherein said sleeve means includes means for stopping the movement of said ring means in an axial direction outwardly towards said face.

11. A system according to claim 10, wherein said sleeve means is a cylindrical sleeve member having opposed first and second annular edges, said first annular edge being spaced axially inwardly from said face of said cell and said second annular edge lying substantially in the same plane as said face of said cell, and said means for stopping is an annular flange extending radially inwardly from the inner surface of said sleeve member, generally at said second annular edge, said annular flange having a stop surface substantially parallel to said plane of said second annular edge and spaced axially inwardly from said face, said stop surface being in pressing contact with said ring means, said annular flange being adapted to press said film means to said body at said second portion of said annular wall.

12. A system according to claim 11, wherein said ring means is a cylindrical ring member having opposed first and second annular ends, spaced from said face, said first annular end being spaced at a greater distance from said face than said second annular end and disposed between said first and second annular edges of said sleeve member.

13. A system according to claim 12, wherein said means for limiting is wherein said first portion of said annular wall of said body has an outward taper from said second rim and the inner surface of said ring member has a mating outward taper from said second annular end to said first annular end.

14. A system according to claim 8, wherein said means for removably connecting said ring means to said body is at least one annular bead extending radially inwardly from said ring member and at least one annular slot formed in said annular wall of said body, said at least one bead being adapted to snap into said annular slot over said film skirt.

15. A system according to claim 14, wherein said at least one annular bead is two spaced annular beads and said at least one annular slot is two spaced annular slots adapted to receive said two annular beads with said film skirt.

16. A system according to claim 15, wherein said means for removably connecting said sleeve means to said body is a circular bead extending radially inwardly from said first annular rim of said sleeve member and a circular slot formed in said annular wall of said body, said circular bead being adapted to snap into said circular slot over said film skirt.

17. A system according to claim 5, wherein said flexible ring means is made of polyethylene.

18. A system according to claim 5, wherein said sleeve means is semi-rigid.

19. A system according to claim 1, wherein said sample material is a powder.

20. A system according to claim 1, wherein said sample material is a liquid.

21. A system according to claim 1, wherein said sample material is a gas.

22. A system according to claim 11 further including an annular lip extending radially inwardly from said second annular edge of said annular flange of said sleeve member and said rim portion of said body forming an annular bevel adapted to receive said annular lip.

23. A method for mounting film to a sample holder body adapted to hold a sample for X-Ray analysis which comprises:
(a) placing in an upward disposition an unloaded, substantially cylindrical sample holder body having a substantially cylindrical wall forming a cell, said wall having an outward taper extending from the upper rim of said wall downwardly for a portion of the wall;
(b) positioning a single layer sheet of thin transparent plastic film across the open face of the cell defined by the upper rim of the cylindrical wall;
(c) drawing the skirts of the film downwards around the outer annular surface of the cylindrical wall of the holder body;
(d) gently sliding a flexible, thin-walled substantially cylindrical ring member tapered to match the taper of the tapered wall portion of the sample holder body around the skirt of the sheet of film and around the upper rim of the holder body;
(e) gently sliding the ring member, which has a circumferential bead at its leading edge, along the tapered wall of the holder body and over the film skirt and forcing the flexible ring member to expand slightly;
(f) gently drawing the film inwardly from the face of the holder body along the annular surface of the holder body and so drawing the film taut across the face of the holder;
(g) positioning a circumferential ring bead of the ring member into connection with a circumferential locking groove formed in the annular surface of the holder body and locking the ring member and the film skirt to a first portion of the annular surface of the holder body;
(h) passing a substantially cylindrical sleeve member leading with a circumferential sleeve bead over the face of the cell and the annular surface of the holder body and over the ring member with the inner surface of the sleeve member spaced slightly radially outwardly from the outer surface of the ring member;
(i) pressing the skirt of the film to a vertical portion of a second portion of the annular surface of the holder body axially inwardly past the tapered portion of the annular surface and drawing the film skirt more tautly around the annular wall of the holder body during the positioning of the sleeve member; and
(j) locking the sleeve member and the film skirt to the holder body by snapping the sleeve bead into a second groove formed in the annular surface of the holder body; and simultaneously pressing the annular inner surface of an inwardly radially extending flange of the sleeve member against the film skirt that extends over a third portion of the annular surface of the holder body between the rim of the holder body and the ring member, and also thus preventing the ring member from moving axially outwardly from its mounted position toward the face of the cell of the holder body.

24. A method according to claim 23, wherein said sample is a powder.

25. A method according to claim 23, wherein said sample is a liquid.

26. A method according to claim 23, wherein said sample is a gas.

27. A method according to claim 23, further comprising the following steps:
between steps (c) and (d)
- (1) sliding a flexible O-ring over the outer annular surface of the holder body and pressing the film skirt to the annular surface of the holder body and drawing the skirt of the film tautly across the face of the holder body; and
- (2) snapping the O-ring and the film skirt into an annular O-ring groove formed in the annular wall of the holder body.

28. A method according to claim 27, wherein the sample is a liquid impregnated into a piece of material.

29. An assembly system for mounting film across the cell face of a holder body of a film locking system that includes an inner substantially cylindrical flexible ring member and an outer sleeve member having a radially inwardly extending flange portion, said holder body having a cell face defined by an annular rim,
- a block member forming first and second vertical substantially cylindrical holes having first and second inner annular surfaces respectively and horizontal first and second top openings respectively, said first inner annular surface being adapted to hold said holder body in a vertical position in said first hole and said second inner annular surface being adapted to hold said sleeve member in a vertical position in said second hole,
- first annular shoulder means extending radially inwardly from said first annular surface for supporting said annular rim of said holder body wherein a portion of said holder body extends upwards past said first top opening,
- second annular shoulder means extending radially inwardly from said first annular surface for supporting said ring member when said ring member is mounted to said holder body and said holder body is supported by said first shoulder means, said second shoulder being disposed proximate to and above said first shoulder, and
- stop means extending radially inwardly from said second annular inner surface for supporting said flange portion of said sleeve member and at least a portion of said annular rim of said holder body, wherein a portion of said holder body and a portion of said sleeve member extend above said second top opening.

30. An assembly system according to claim 29 further including an O-ring and a third annular shoulder means extending radially inwardly from said first annular surface for supporting said O-ring when said holder body is supported by said first shoulder means, said third shoulder means being disposed spaced from and above said second shoulder means.

31. An assembly system according to claim 30, further including a recess means formed in said block member around said first top opening, said recess means being for positioning a sheet of said film.

32. An assembly system according to claim 31, further including first and second means for passing air trapped in said first and second holes from the bottom of said hole during insertion of said holder body and said film into said first and second holes respectively.

33. An assembly system according to claim 32, further including a cap snap-mounted to the top of a holder body positioned in said second hole after placement of said sample in said holder body and a cap lifting means for removing said cap from said holder body when the X-Ray analysis of said sample has been completed, said cap lifting means including a lifting apparatus having a base and an arm rotatably connected to said base at one end and removably connected to a biasable gripper at the other end, said gripper being capable of grasping said cap; said cap lifting means further including a hold-down means capable of being slidably mounted to and braced with said block member, said hold-down means being for holding down said holder body at said annular rim during the lifting of said cap from said holder body.

34. A method for mounting a sheet of film to a sample holder body capable of holding a sample for X-ray analysis, by use of an assembly block forming vertical first and second vertical wells wherein said first well includes a first annular shoulder and a second annular shoulder disposed proximate to and above the first shoulder and the second well includes an annular stop, which comprises:
- (a) placing a cylindrical ring member into the first well and setting the bottom rim of the ring member on the first annular shoulder;
- (b) placing a single layer sheet of transparent plastic film in a film recess formed around the top of the first well;
- (c) inserting a sample holder body bottom annular rim downwards into the first well against the sheet of film and pressing the holder body and the film downwards into the first well and tautening the film across the face of the bottom rim of the holder body;
- (d) snapping a annular ring slot in the holder body into connection with the annular bead of a ring member so that the ring member is connected to the holder body and the skirt of the film is pressed against a first portion of the outer surface of the holder body by the ring member and by the bead of the ring member;
- (e) removing the holder body with the partially secured mounted film with the ring member from the first well by grasping the portion of the holder body extending above the top surface of the assembly block;
- (f) placing a cylindrical sleeve member into the second well of the assembly block against the annular stop in the second well;
- (g) inserting the holder body with the partially secured film and ring member film face downwards into the second well so that the upper and lower portions of the sleeve member press the skirt of the film against the second and third portions of the outer surface of the holder body respectively above and below the ring member and further tautening the film across the face of the holder;
- (h) snapping the annular sleeve slot in the sample holder body into connection with a annular bead of the sleeve member so that the sleeve member is connected to the holder body and the skirt of the film is pressed against the second and third portions of the outer surface of the holder body by the sleeve member and by the bead of the sleeve member; and (i) removing the holder body with the fully secured mounted film from the second well by holding the portion of the holder body or the sleeve member extending above the top surface of the assembly block.

35. A method according to claim 34, wherein said second well includes
a third annular shoulder, further including the following steps in substitution for step (a) above:
(1) placing an O-ring into the first well and setting the O-ring in the third annular shoulder;
between steps (b) and (c) above insert the following steps:
(2) inserting the sample holder bottom rim downwards into the first well against the sheet of film and pressing the holder body and the film into the first well and tautening the film across the face of the bottom rim of the holder body;
(3) removing the holder body with the partially secured mounted film with the O-ring from the first well; and
(4) adding step (a), which was removed above.

36. A method according to claim 35, wherein two film sheets sandwiching a sample filter can be mounted to the holder body by adding to step (b) above the following step:
(b') placing a second single layer sheet of film in the film recess around the first well of the assembly block.

* * * * *